United States Patent [19]

Shturman

[11] Patent Number: 5,360,432
[45] Date of Patent: Nov. 1, 1994

[54] ABRASIVE DRIVE SHAFT DEVICE FOR DIRECTIONAL ROTATIONAL ATHERECTOMY

[75] Inventor: Leonid Shturman, Minneapolis, Minn.

[73] Assignee: Shturman Cardiology Systems, Inc., Minneapolis, Minn.

[21] Appl. No.: 992,415

[22] Filed: Dec. 17, 1992

Related U.S. Application Data

[63] Continuation-in-part of Ser. No. 967,765, Oct. 28, 1992, and a continuation-in-part of Ser. No. 962,634, Oct. 16, 1992, Pat. No. 5,312,427.

[51] Int. Cl.$^5$ ............................................. A61B 17/32
[52] U.S. Cl. .................................. 606/159; 606/170; 606/180
[58] Field of Search ............... 606/159, 170, 171, 180; 604/22, 96

[56] References Cited

U.S. PATENT DOCUMENTS

| Re. 33,569 | 4/1991 | Gifford, III et al. . |
| Re. 33,911 | 5/1992 | Samson et al. . |
| 4,445,509 | 5/1984 | Auth . |
| 4,679,557 | 7/1987 | Opie et al. . |
| 4,781,186 | 11/1988 | Simpson et al. . |
| 4,794,931 | 1/1989 | Yock . |
| 4,887,606 | 12/1989 | Yock et al. . |
| 4,917,097 | 4/1990 | Proudian et al. . |

(List continued on next page.)

FOREIGN PATENT DOCUMENTS

| 0359447 | 3/1990 | European Pat. Off. . |
| 9004657 | 8/1990 | WIPO . |
| 9101813 | 3/1991 | WIPO . |
| 9105844 | 8/1991 | WIPO . |

OTHER PUBLICATIONS

Gilmore, H. W., et al, "Instrumentation," *Operative Density*, 4th Ed., Ch. 4, pp. 55, 64–73, The C. V. Mosby Company, 1982.

(List continued on next page.)

Primary Examiner—Stephen C. Pellegrino
Assistant Examiner—William Lewis
Attorney, Agent, or Firm—Gregory P. Kaihoi

[57] ABSTRACT

An abrasive drive shaft atherectomy device for removing stenotic tissue from an artery. The device includes a rotational atherectomy apparatus having a flexible, elongated drive shaft having a central lumen and a segment, near its distal end, coated with an abrasive material to define an abrasive segment. In one embodiment the device includes a special guide wire having a generally straight proximal portion, a distal end portion, and a flexible intermediate positioning segment. The positioning segment has a predetermined curved shape such that when the abrasive segment of the drive shaft is advanced over the guide wire to a position along the curved positioning segment, such curved segment positions the abrasive segment laterally away from the longitudinal axis of the proximal portion of the drive shaft. In another embodiment a conventional, generally straight guide wire is utilized, along with a separate positioning wire. The positioning wire is slidably secured, at its distal end to the guide wire so that the positioning wire can be moved proximally and distally with respect to the guide wire. The positioning wire includes a distal positioning segment having a predetermined shape. Rather than being advanced over the guide wire, the drive shaft is advanced over the positioning wire. When the drive shaft's abrasive segment is positioned along the predetermined curved shape of positioning wire's positioning segment, the positioning segment positions the abrasive segment laterally away from the guide wire, thus giving control over the lateral position of the burr within the artery. In either embodiment, the device therefore allows selective removal of tissue from one side of an artery, permitting selective treatment of eccentric stenotic lesions without damaging the artery wall, and permitting treatment of lesions generally without blocking blood flow through the artery during use of the device.

47 Claims, 30 Drawing Sheets

U.S. PATENT DOCUMENTS

| | | |
|---|---|---|
| 4,917,103 | 4/1990 | Gambale et al. . |
| 4,926,858 | 5/1990 | Gifford, III et al. . |
| 4,950,277 | 8/1990 | Farr .................................. 606/180 |
| 4,979,951 | 12/1990 | Simpson . |
| 4,984,581 | 1/1991 | Stice . |
| 4,990,134 | 2/1991 | Auth . |
| 5,000,185 | 3/1991 | Yock . |
| 5,007,434 | 4/1991 | Doyle et al. . |
| 5,010,886 | 4/1991 | Passafaro et al. . |
| 5,024,234 | 6/1991 | Leary et al. . |
| 5,029,588 | 7/1991 | Yock et al. . |
| 5,047,040 | 9/1991 | Simpson et al. . |
| 5,053,044 | 10/1991 | Mueller et al. . |
| 5,054,492 | 10/1991 | Scribner et al. . |
| 5,067,489 | 11/1991 | Lind . |
| 5,071,424 | 12/1991 | Reger . |
| 5,074,871 | 12/1991 | Groshong . |
| 5,092,873 | 3/1992 | Simpson et al. . |
| 5,100,424 | 3/1992 | Jang et al. . |
| 5,100,425 | 3/1992 | Fishell et al. ..................... 606/159 |
| 5,217,474 | 6/1993 | Zacca et al. ...................... 606/159 |

OTHER PUBLICATIONS

Gilmore, H. W., et al., *Operative Dentistry*, 4th Ed., pp. 348–351, 353–354, The C. V. Mosby Company, 1982.

"Premier Two Striper® Gingival Curretage," Abrasive Technology Inc., Westerville, Ohio USA.

"Premier Two Striper® Crown & Bridge Techniques," Abrasive Technology, Inc., Westerville, Ohio USA.

Tupac, Robert G., et al, "A Comparison of Cord Gingival Displacement with the Gingitage Technique," *The Journal of Prosthetic Dentistry*, Nov. 1981, vol. 46, No. 5, pp. 509–515.

*Atherectomy, A Physician's Guide*, Strategic Business Development, Inc., Kauai, Hawaii 96714 USA, 1990, pp. 1–114.

Bom, N., et al, "Early and Recent Ultrasound Devices," *International Journal of Cardiac Imaging*, 4:79–88, 1989.

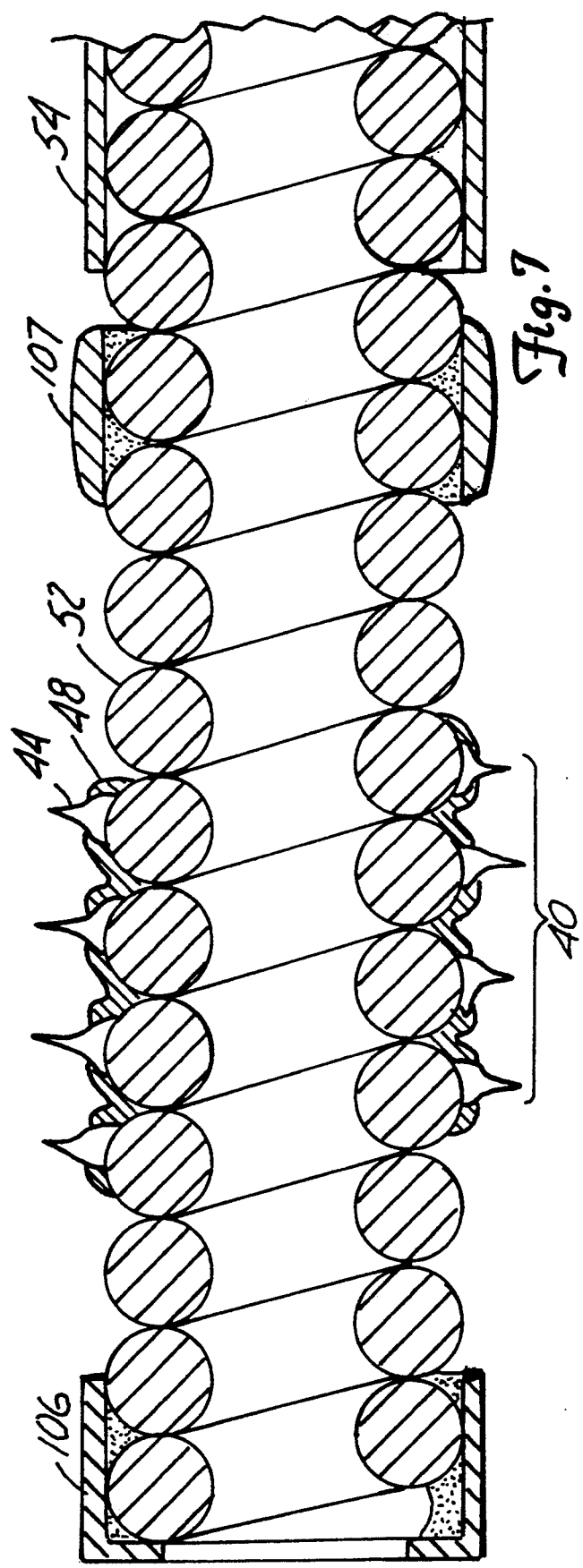

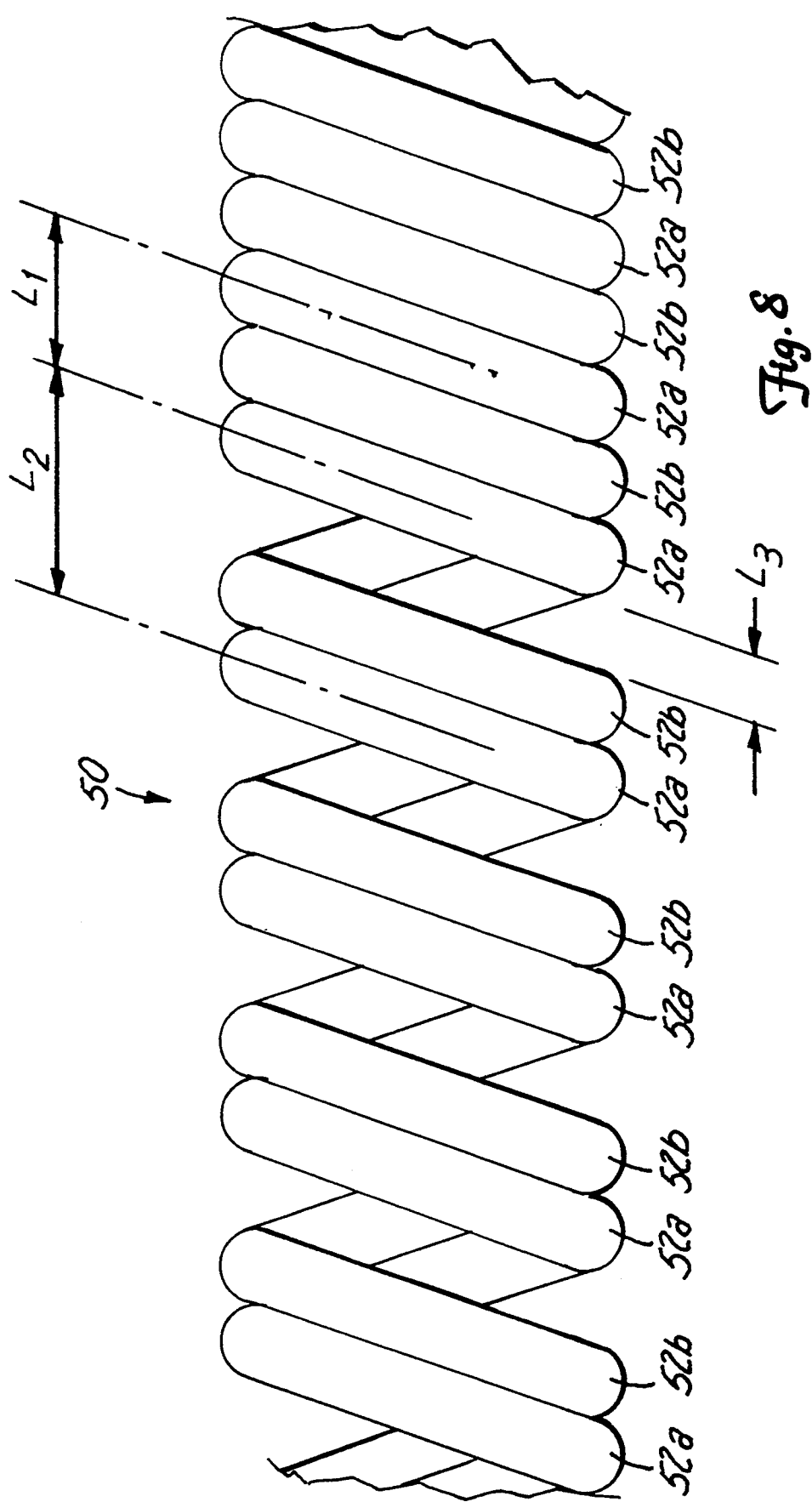

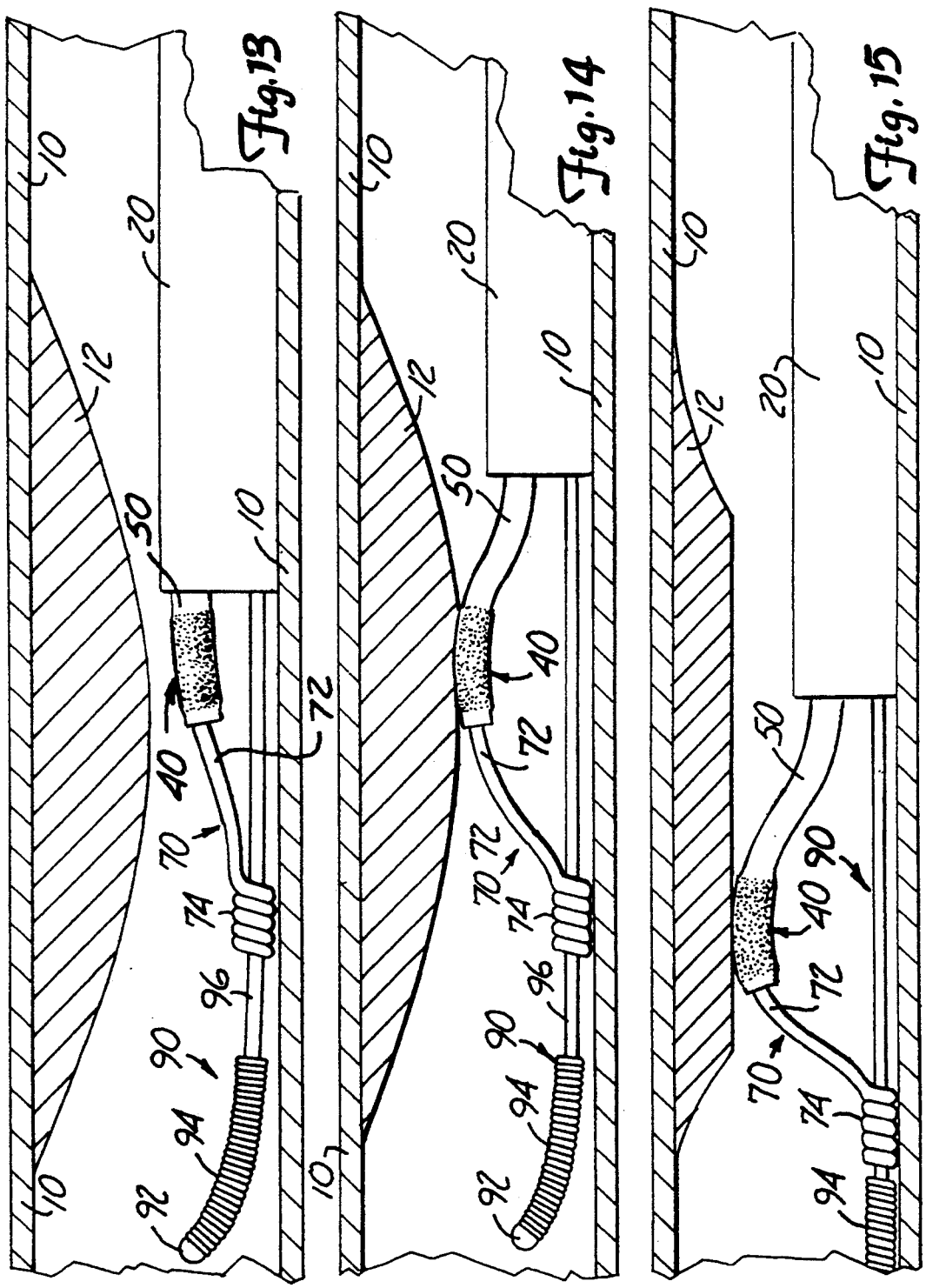

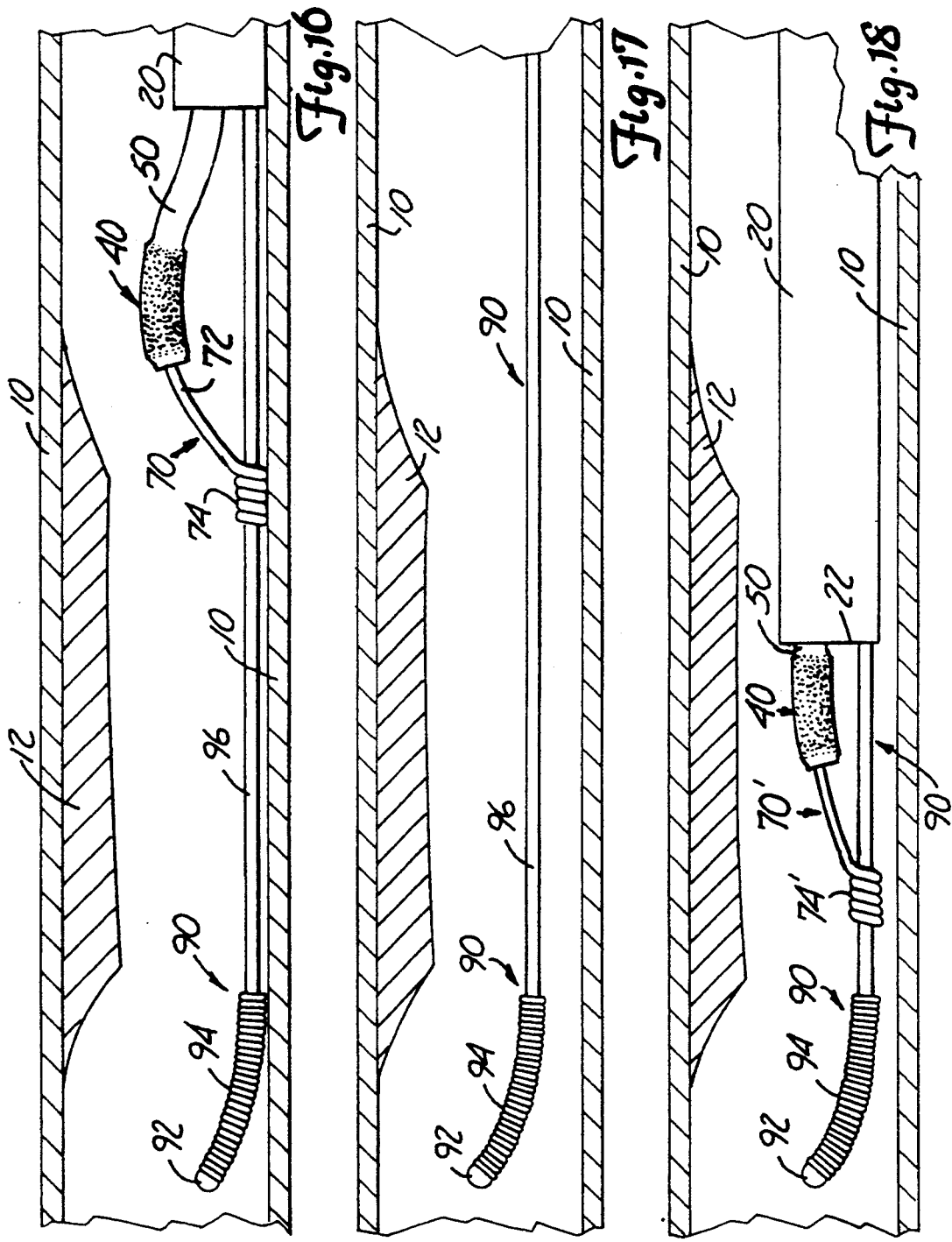

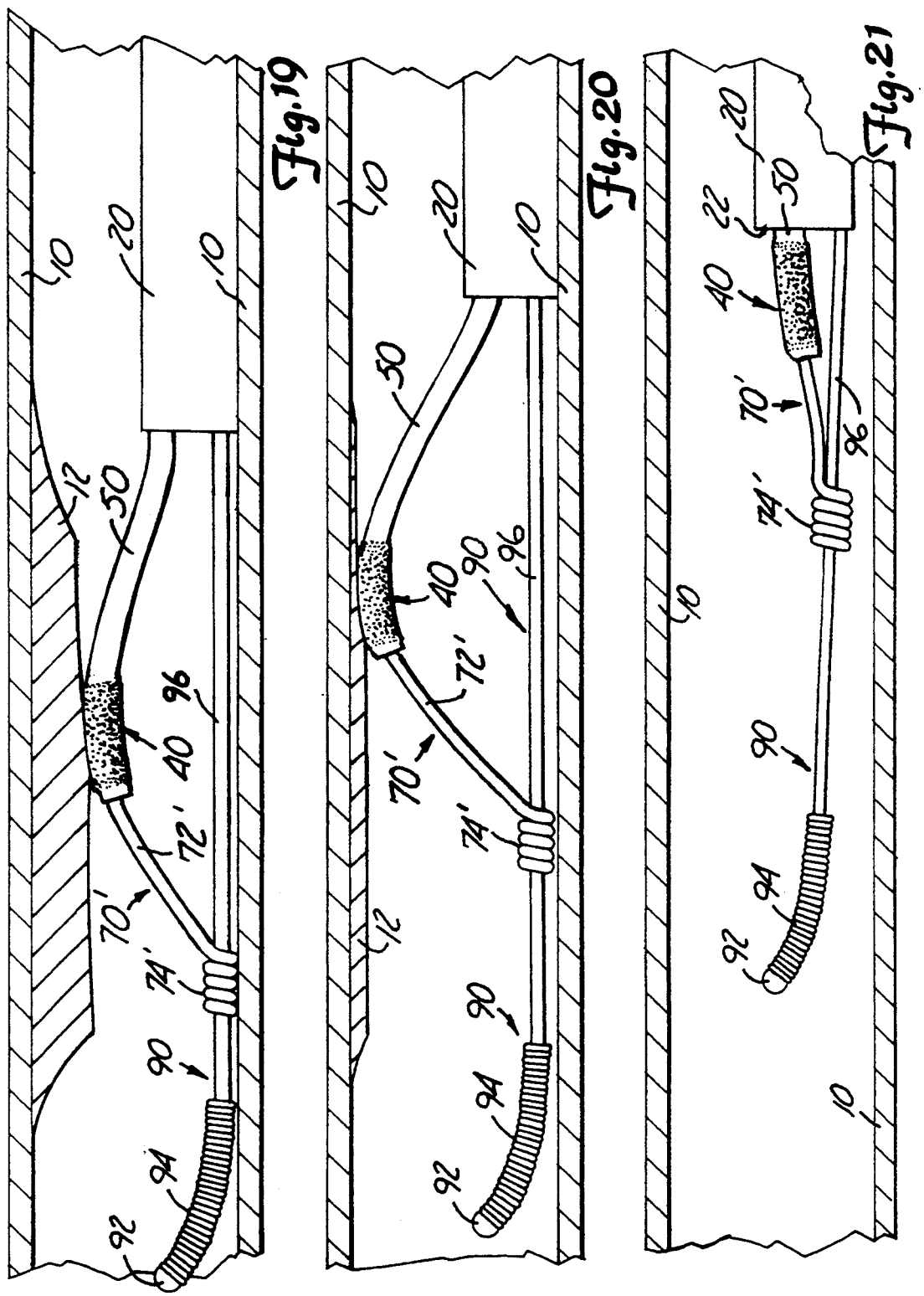

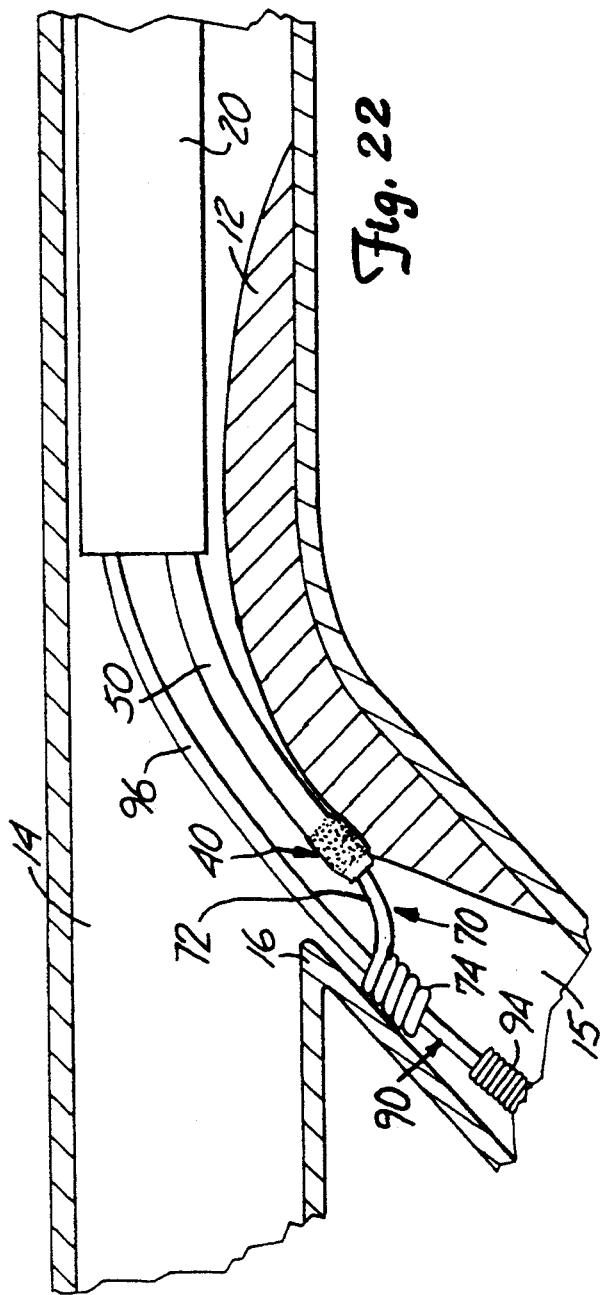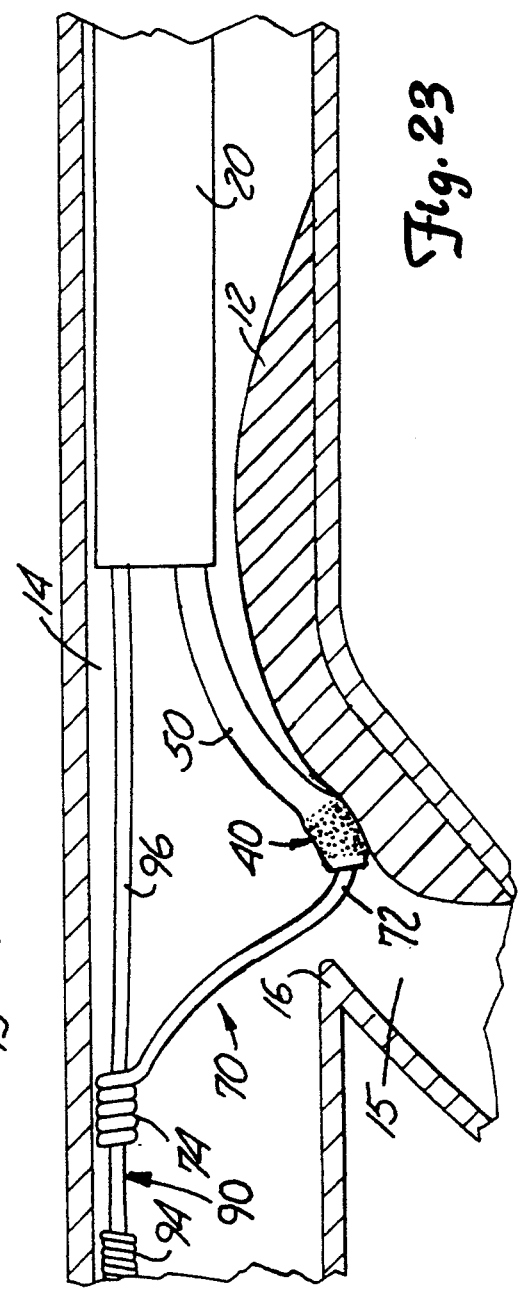

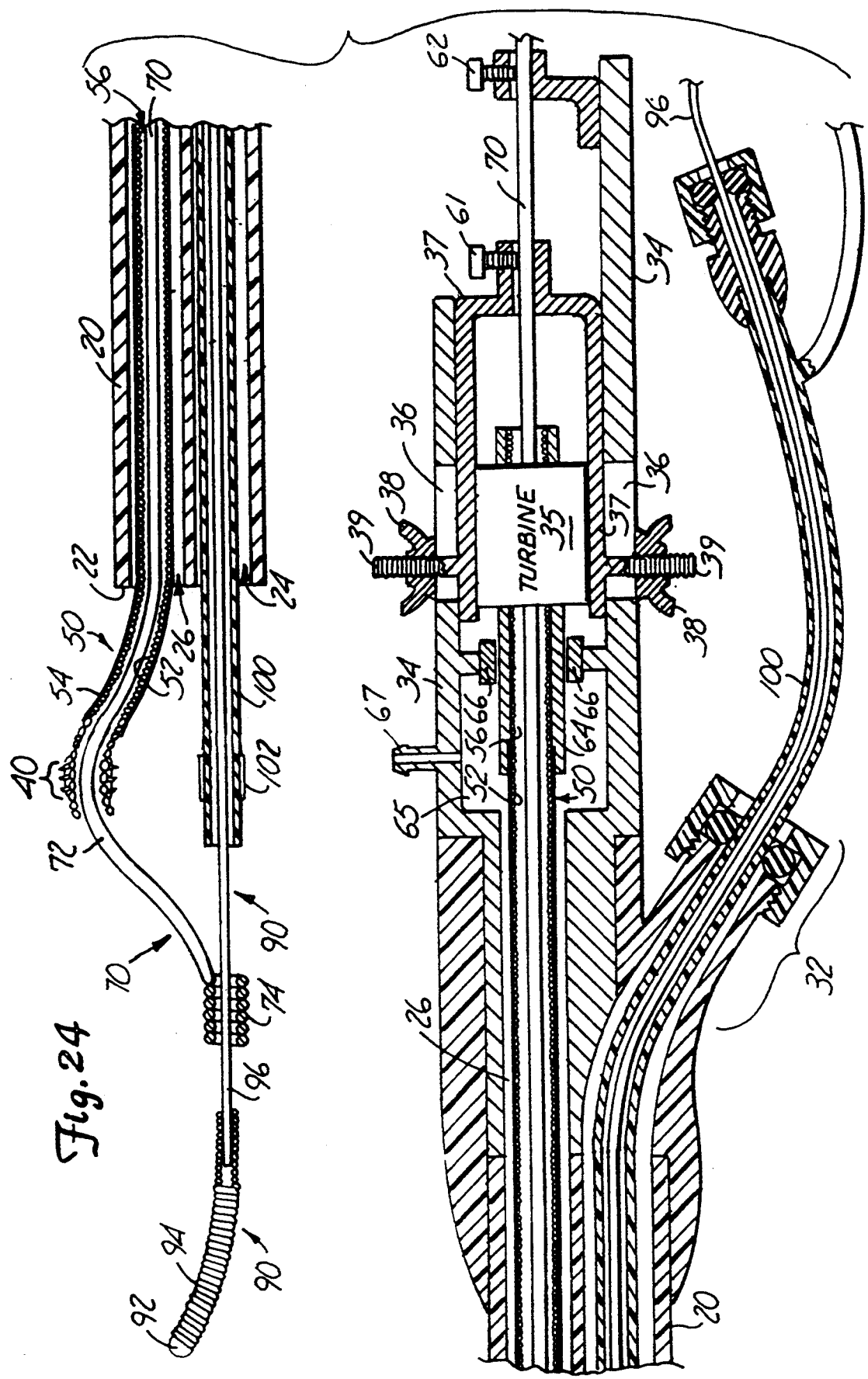

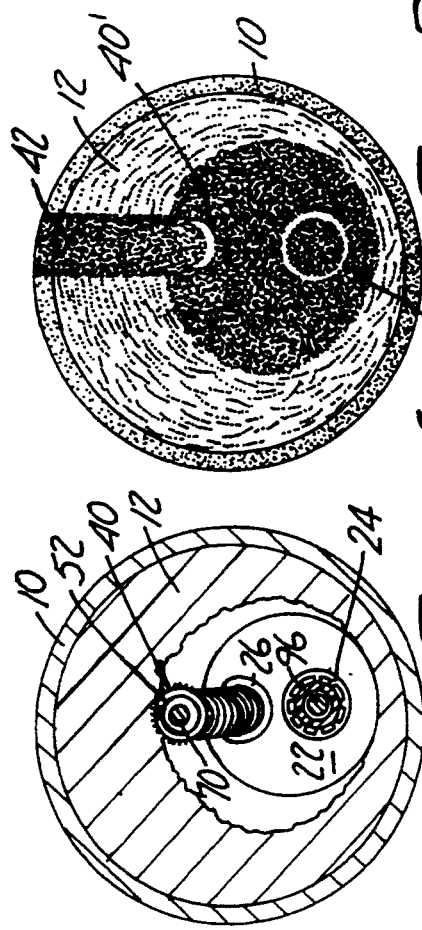
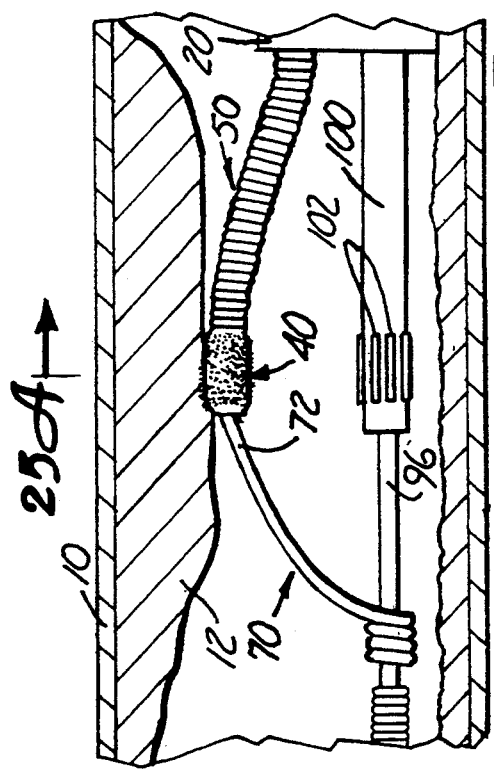

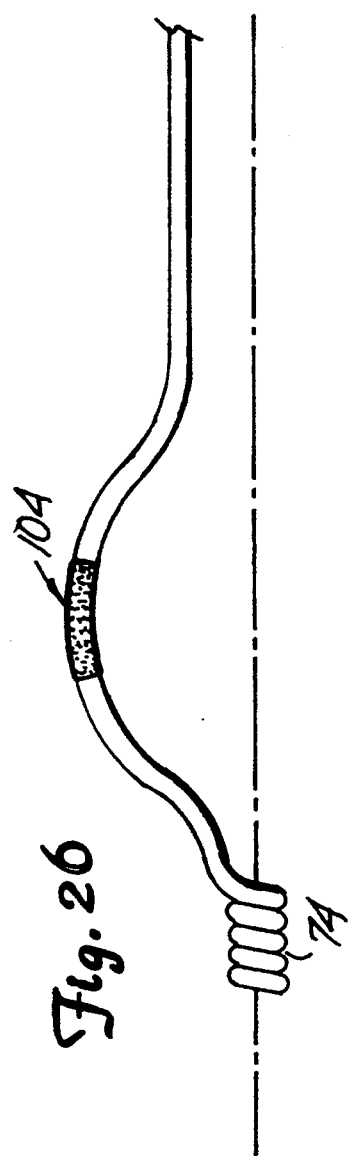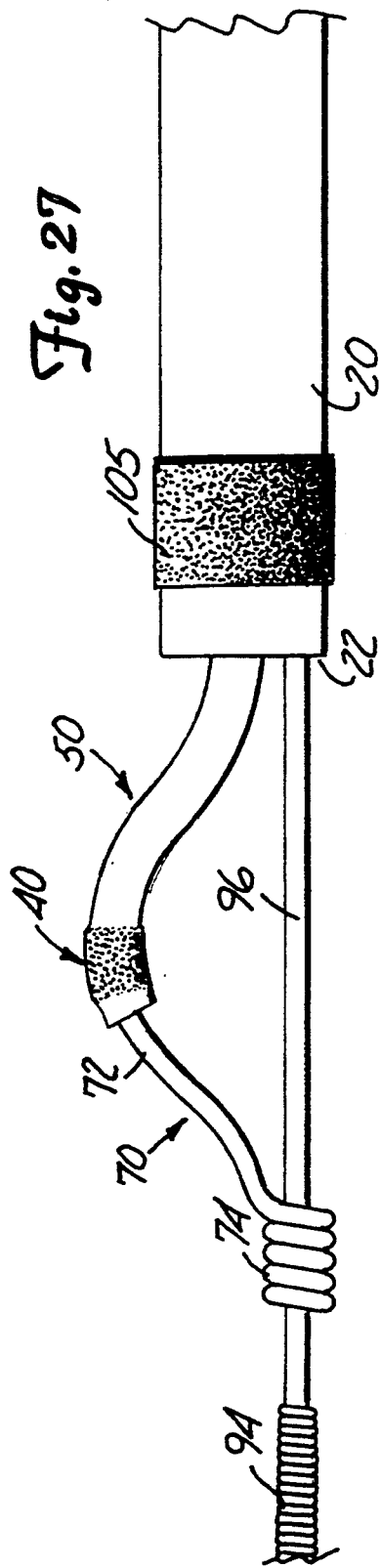

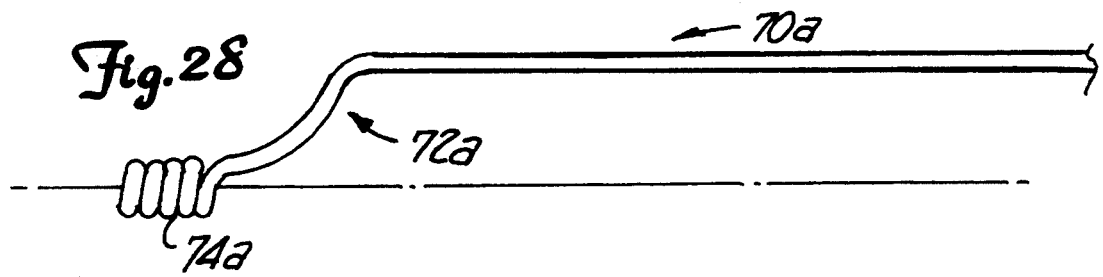
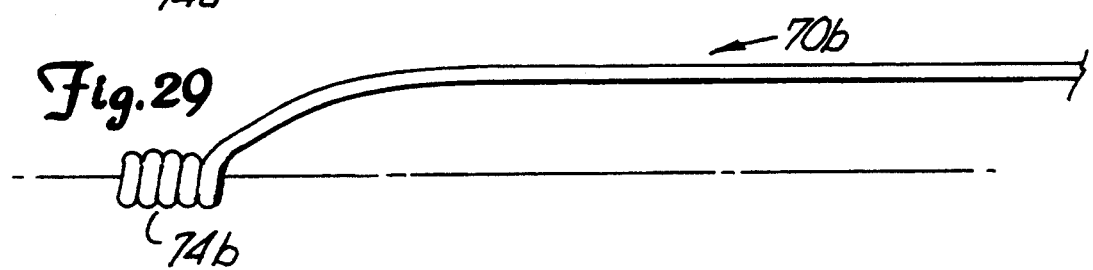
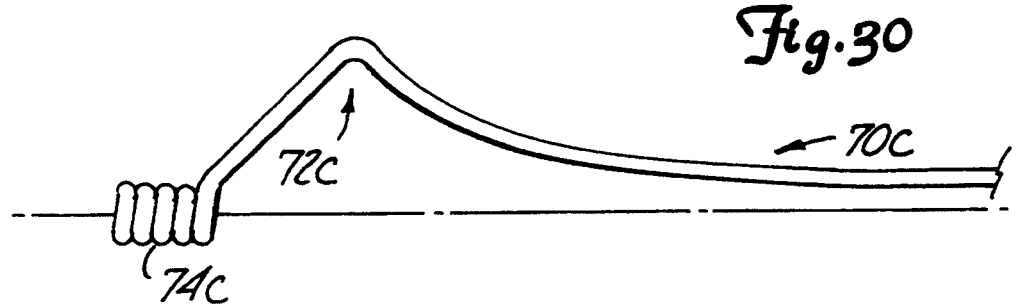
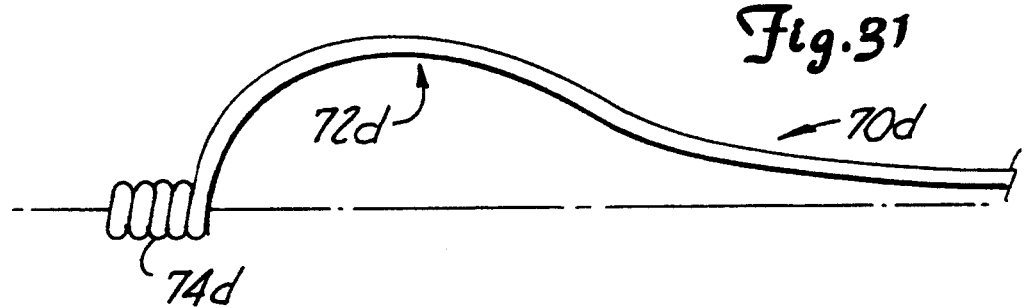
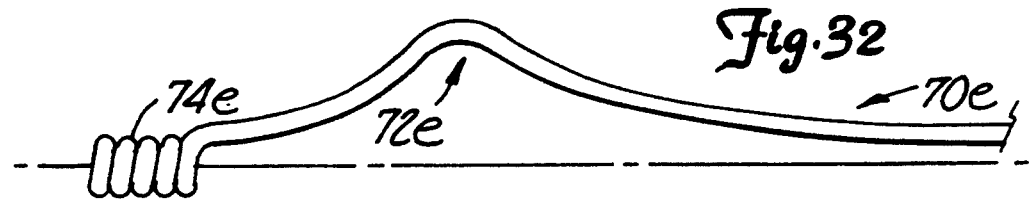

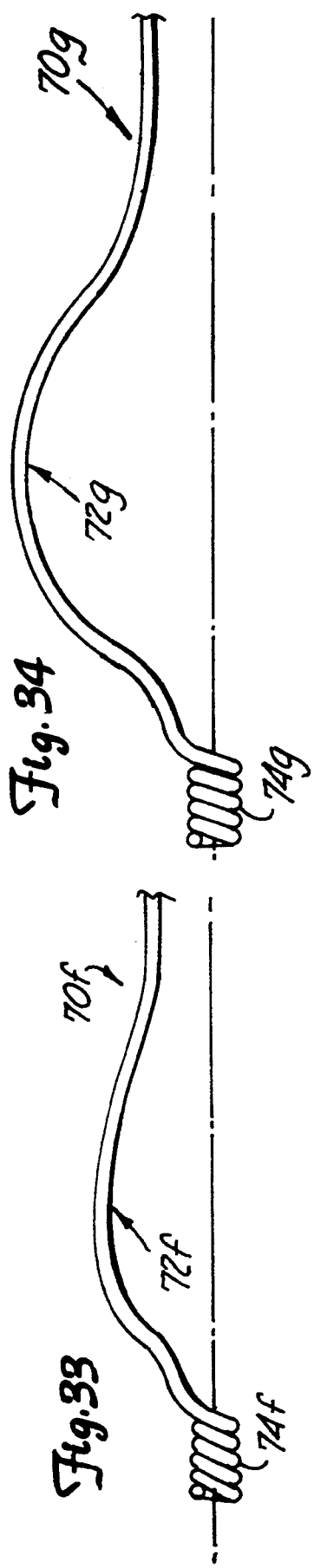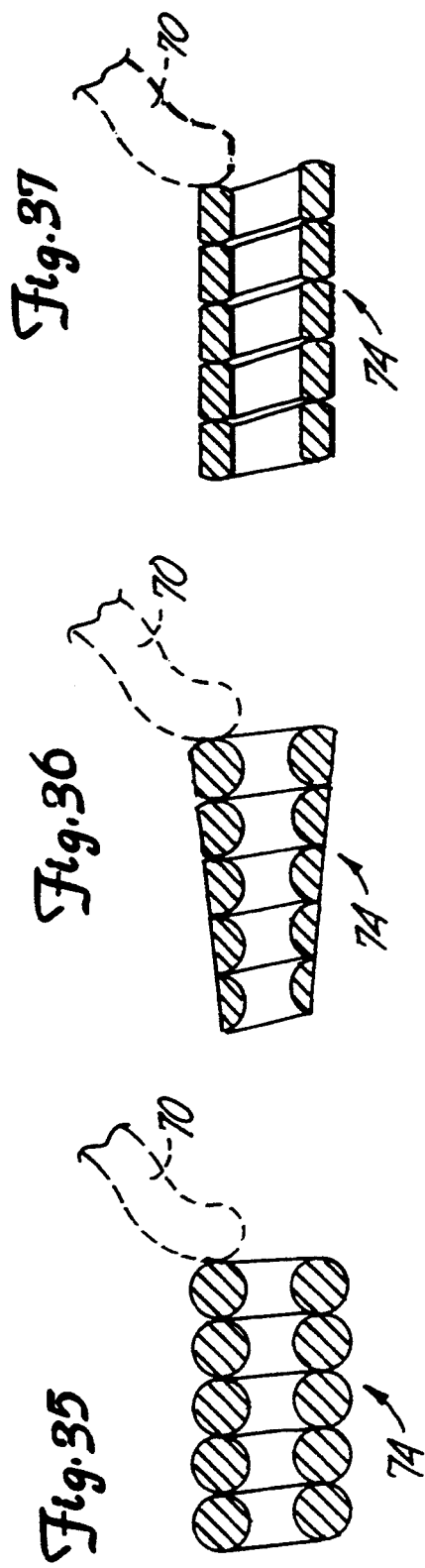

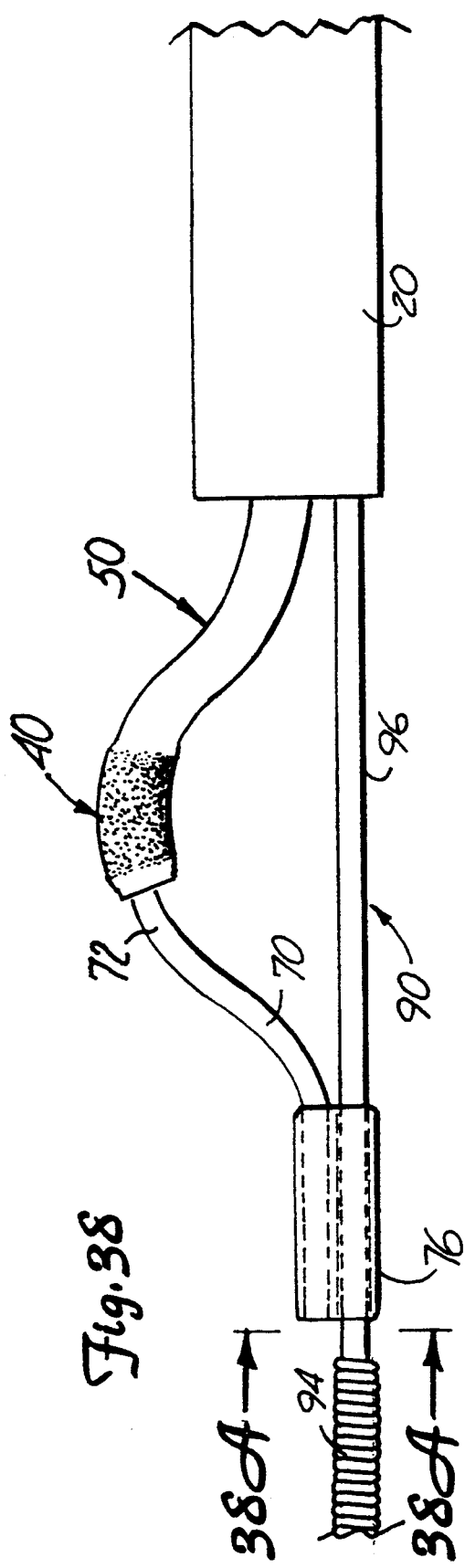
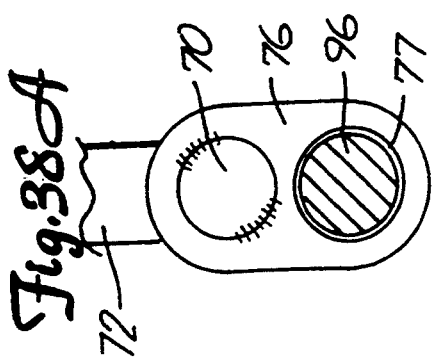

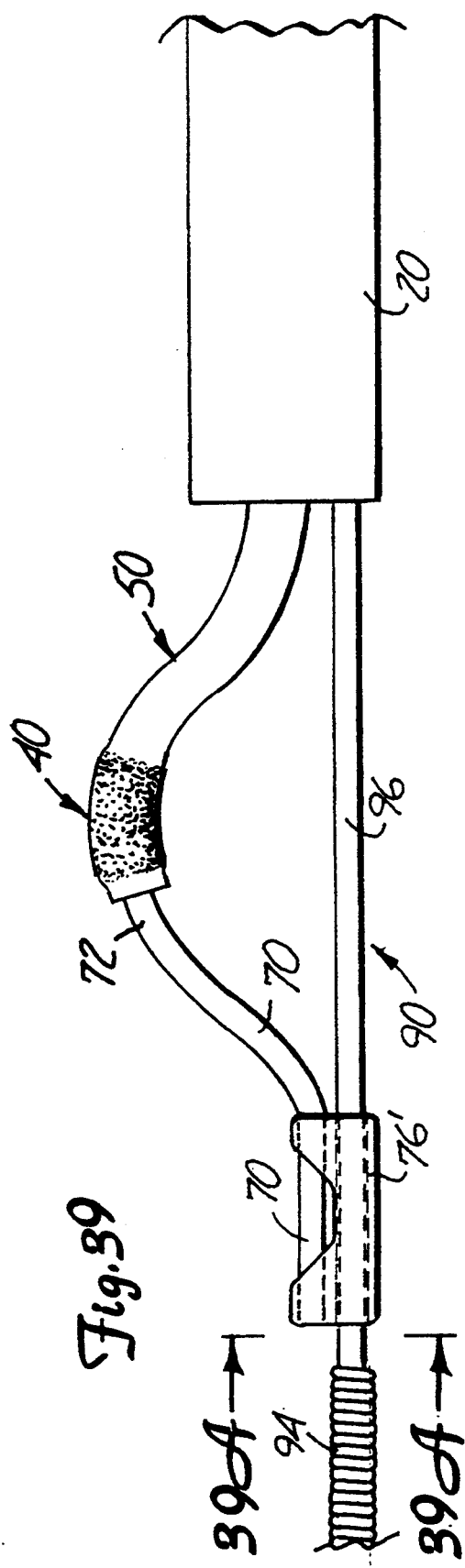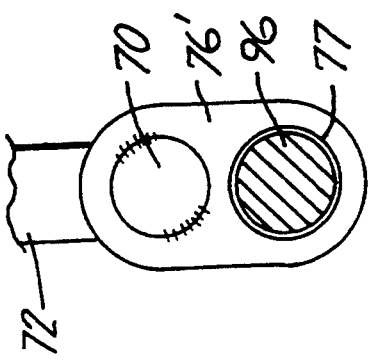

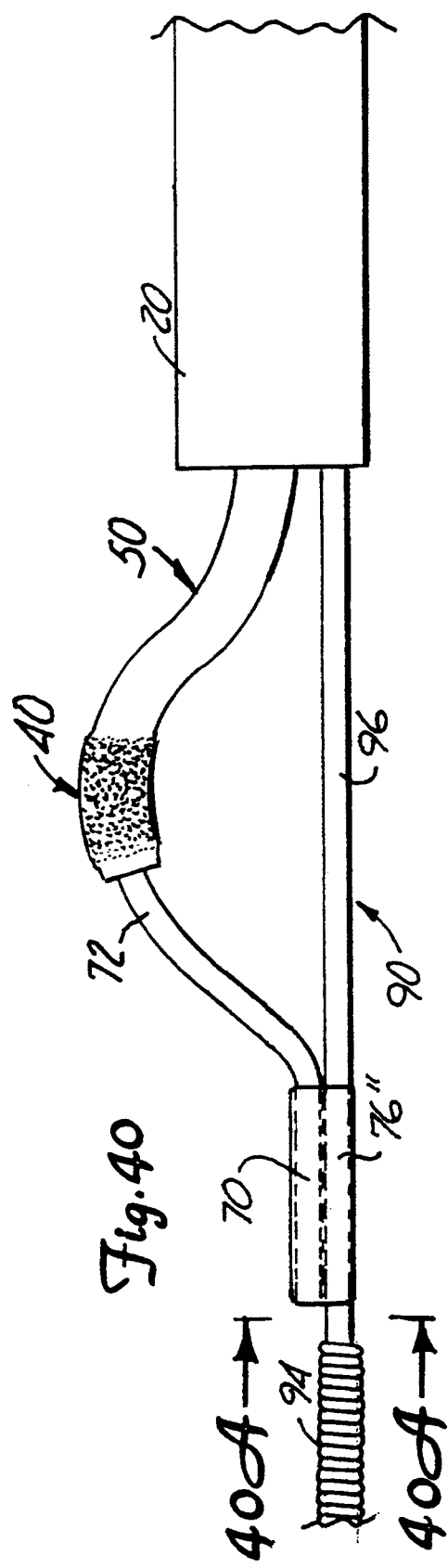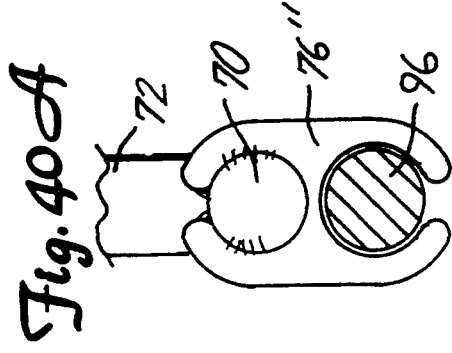

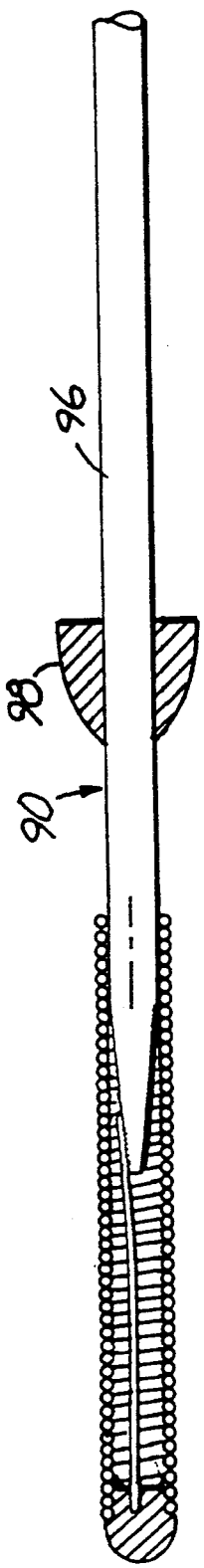
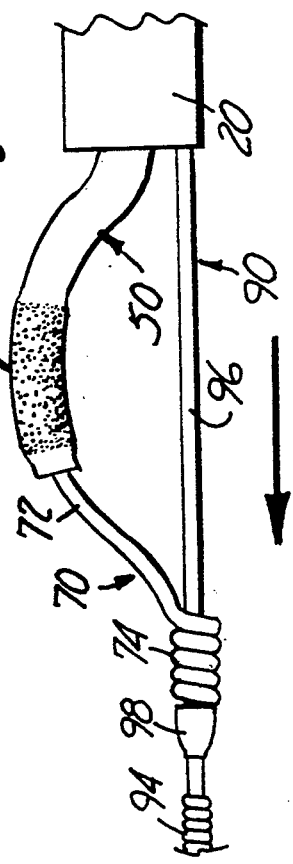
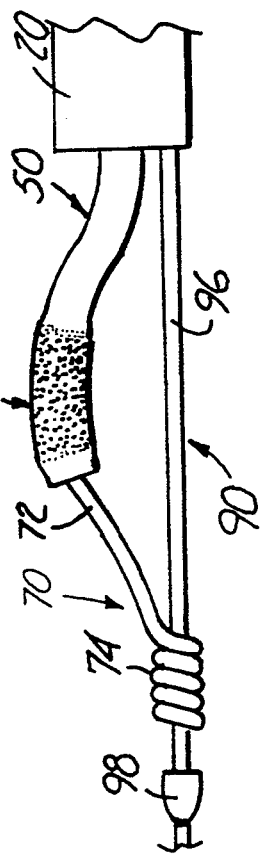

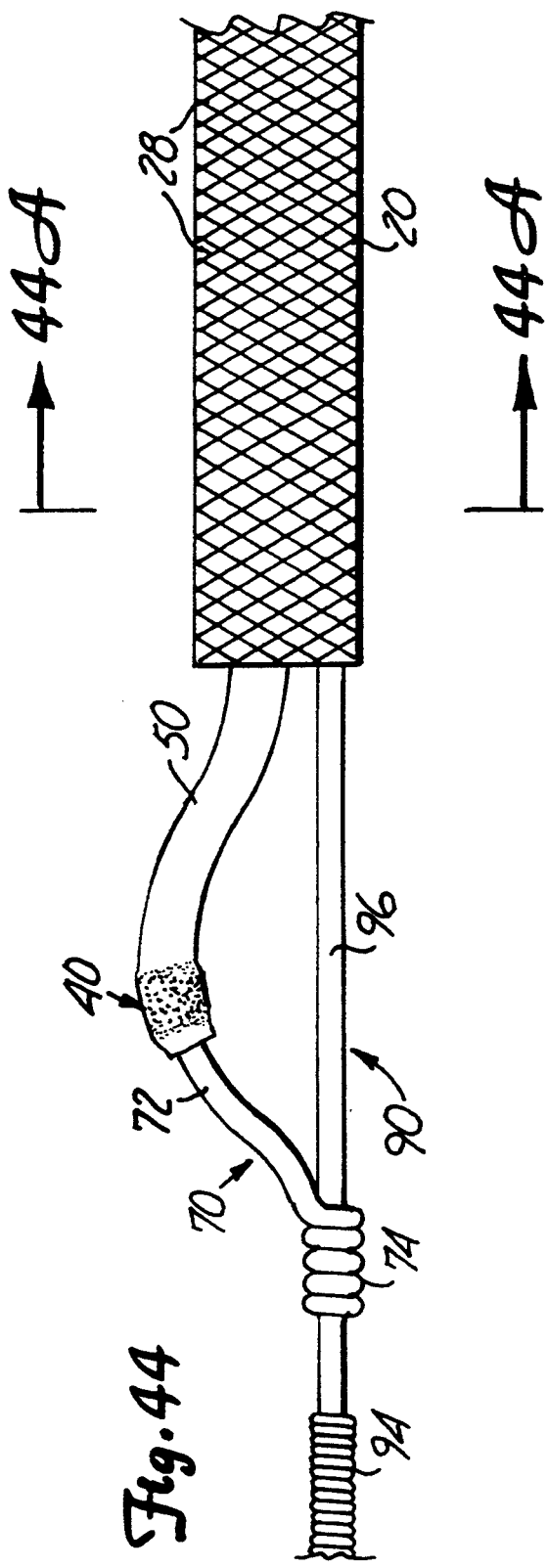
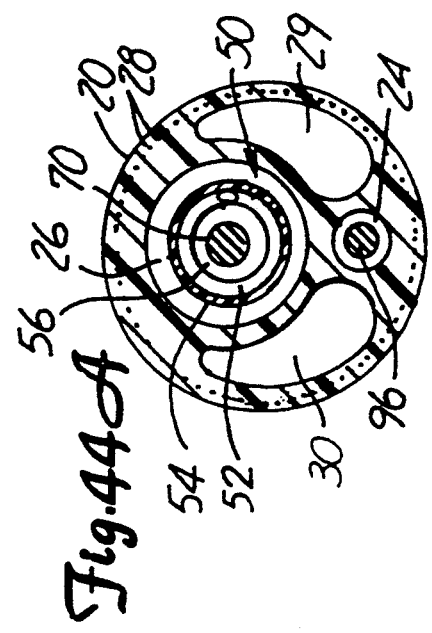

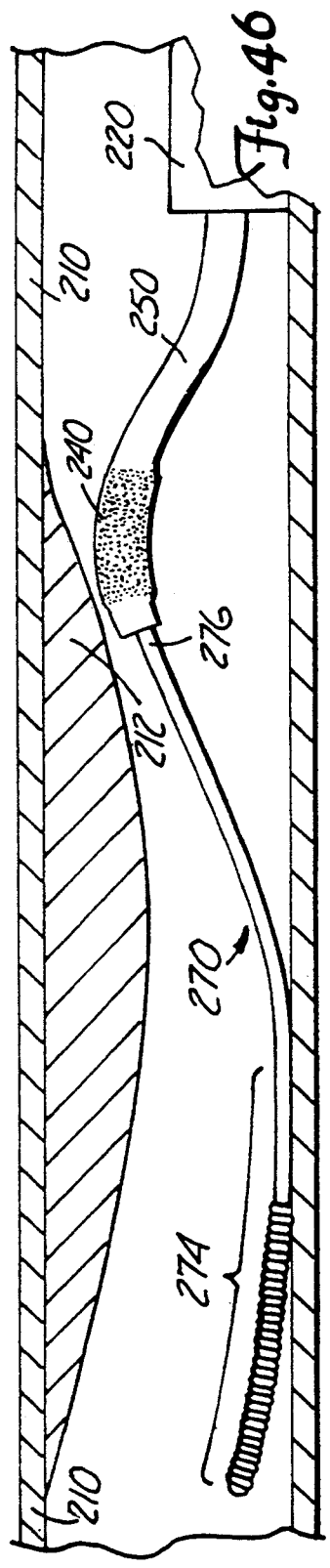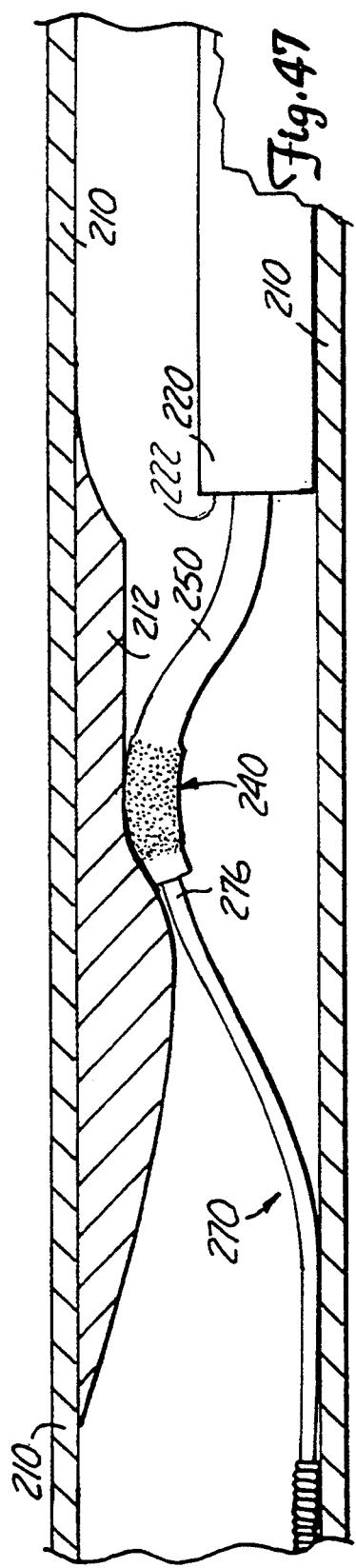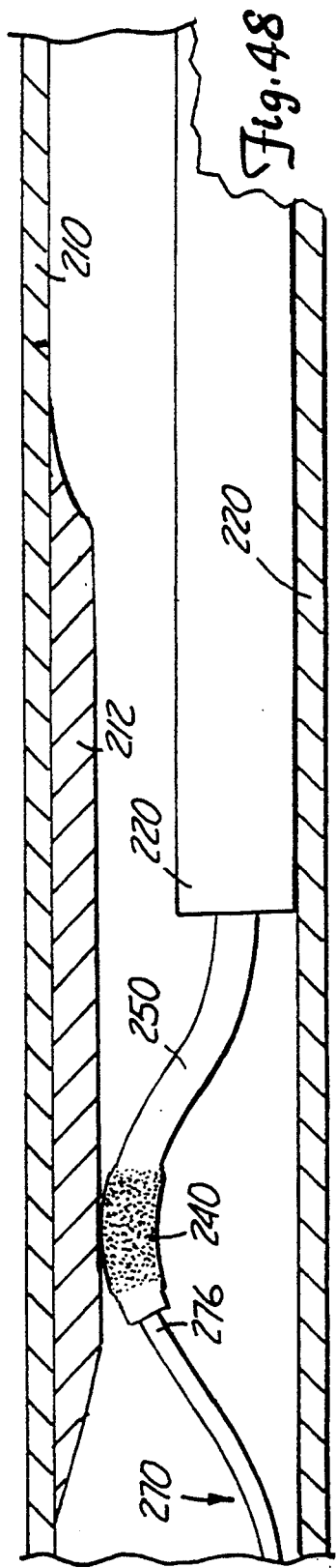

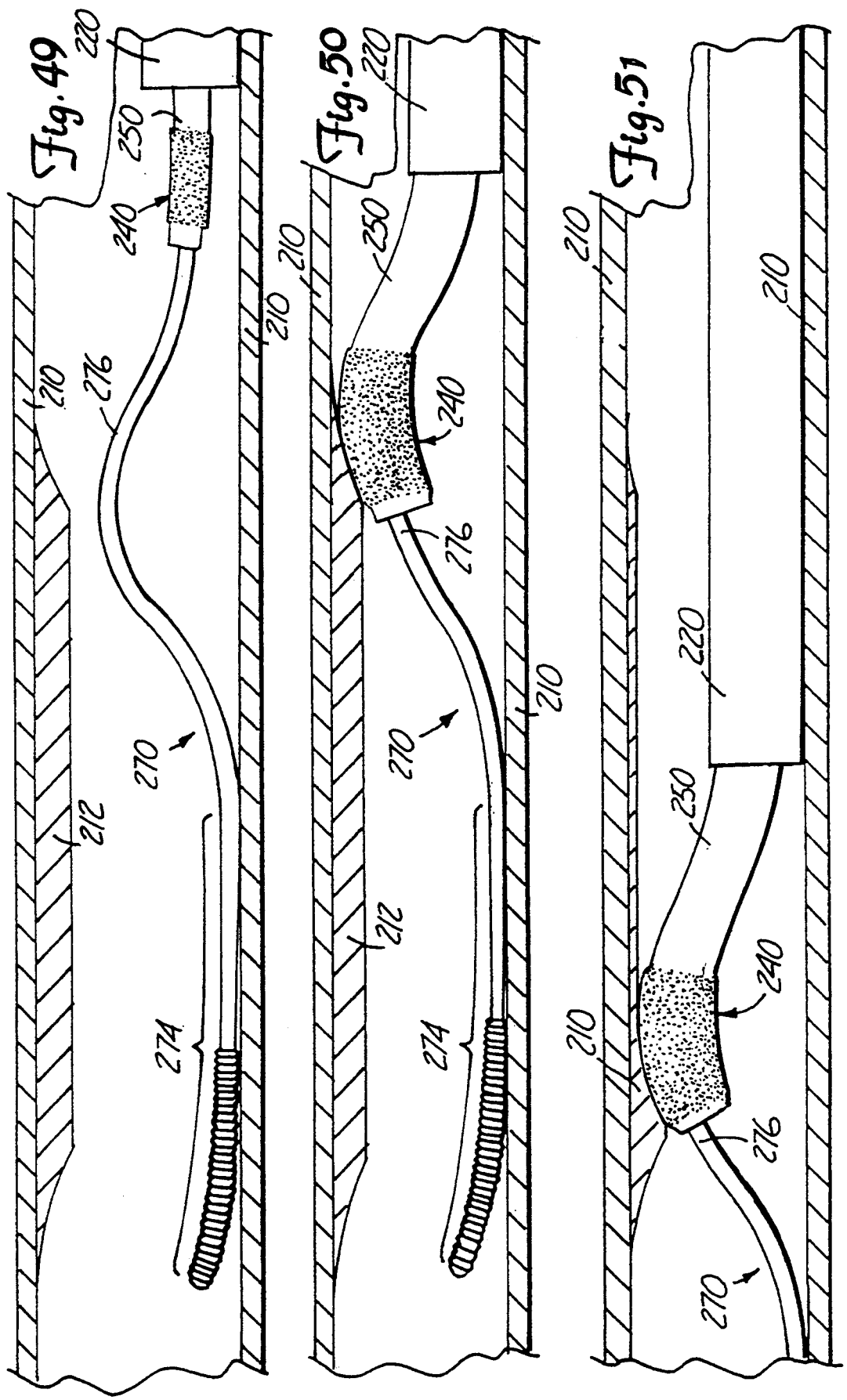

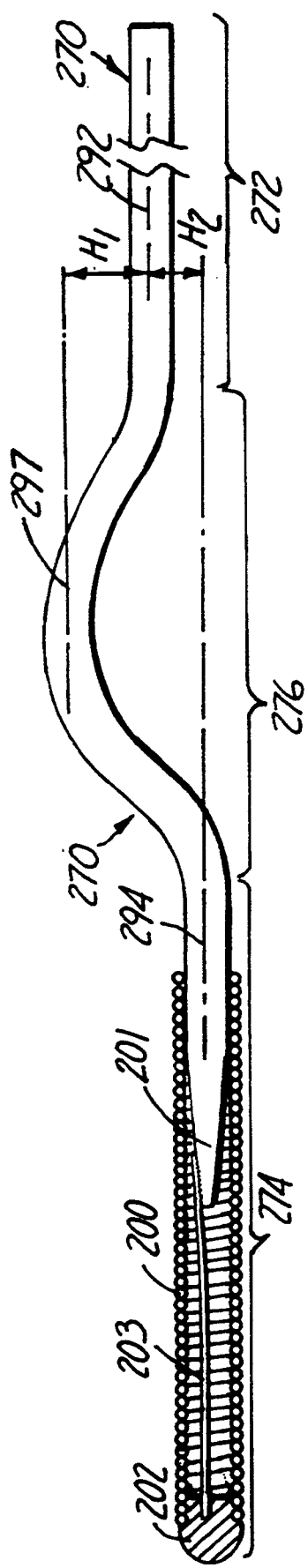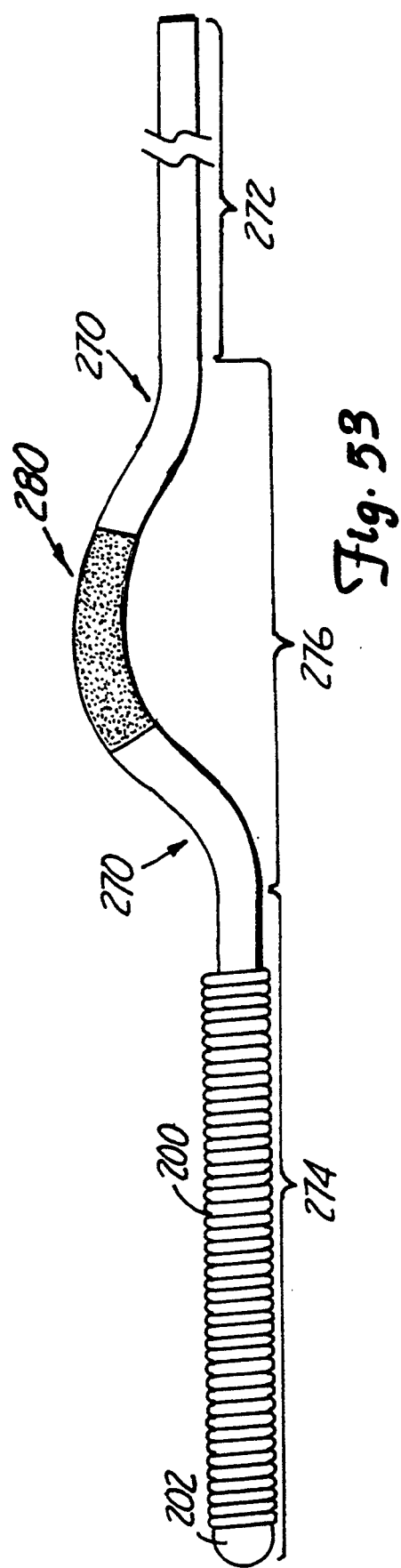

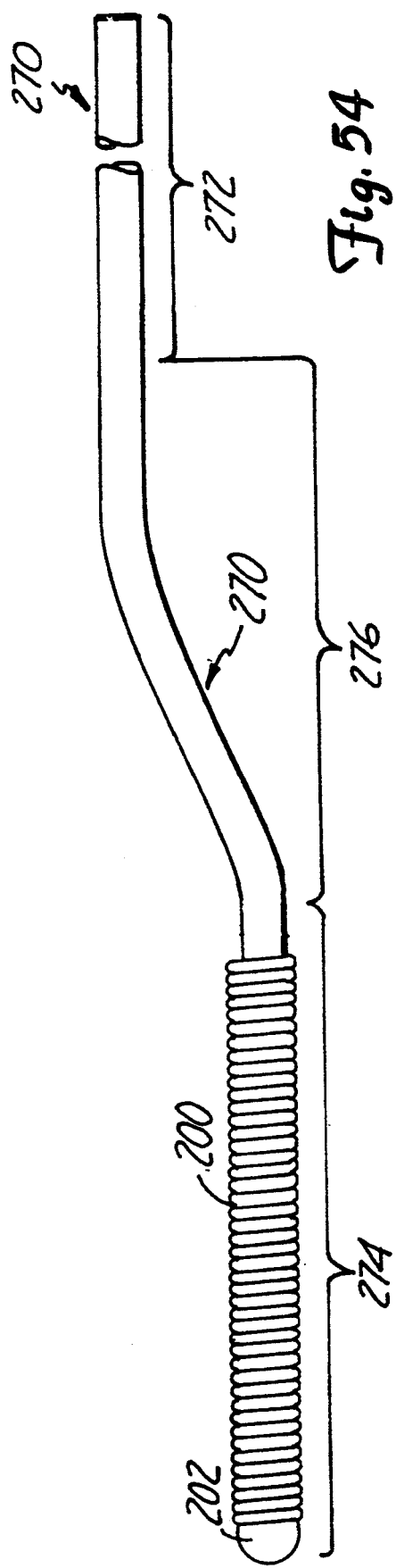
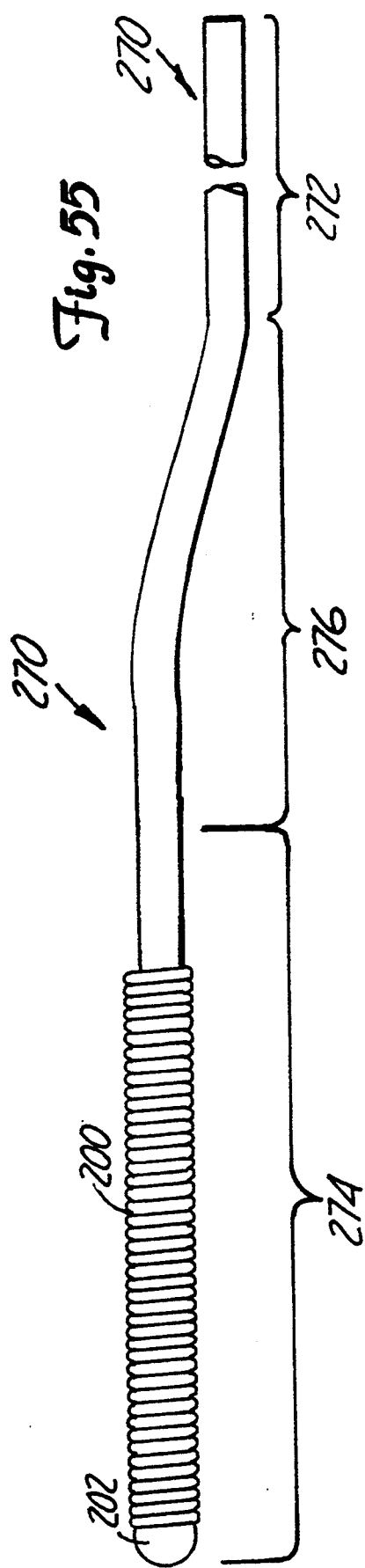

ABRASIVE DRIVE SHAFT DEVICE FOR DIRECTIONAL ROTATIONAL ATHERECTOMY

RELATED APPLICATIONS

This application is a continuation in part of U.S. application Ser. No. 07/967,765, filed Oct. 28, 1992, now pending, and is also a continuation in part of U.S. application Ser. No. 07/962,634, filed Oct. 16, 1992, now U.S. Pat. No. 5,312,427.

FIELD OF THE INVENTION

The invention relates to devices and methods for removing tissue from body passageways, such as removal of atherosclerotic plaque from arteries, utilizing a rotary atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft cholesterol-rich atheromatous material hardens into a calcified atherosclerotic plaque. Such atheromas restrict the flow of blood, and therefore are often referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 5,092,873 (Simpson), a cylindrical housing, carried at the distal end of a catheter, has a portion of its side-wall cutout to form a hollow housing into which the atherosclerotic plaque can protrude when the device is positioned next to the plaque. An atherectomy blade, disposed within the housing, is then advanced the length of the housing to lance the portion of the atherosclerotic plaque that extends into the housing cavity. While such devices provide for directional control in selection of tissue to be excised, the length of the portion excised at each pass of the atherectomy blade is necessarily limited to the length of the cavity in the device-in turn, the length and relative rigidity of the housing limits the maneuverability and therefore the utility of the device in narrow and tortuous passageways such as coronary arteries.

Another approach which solves some of these problems involves the use of a rotating burr covered with an abrasive cutting material such as diamond grit (diamond particles or dust) carried at the distal end of a flexible drive shaft, similar to a dental abrading/polishing tool. Examples of such devices are illustrated in U.S. Pat. No. 4,990,134, (issued to Auth), as well as "Premier Two Striper ® Gingival Curettage" (Abrasive Technology, Inc. 1982); "Premier Two Striper ® Crown & Bridge Techniques" (Abrasive Technology, Inc. 1981); H. Gilmore, et. al, *Operative Dentistry* (C.V. Mosby Company 1982, 4th ed.), pp. 64–65, 69, 348–350; R. Tupac, et al., "A Comparison of Cord Gingival Displacement With the Gingitage Technique," *Journal of Prosthetic Dentistry*, (Nov. 1981, pp. 509–515); and Premier Presents Two Striper ® Dental Diamond Instruments (Abrasive Technology, Inc. 1989). The burr in such devices is rotated at speeds in the range of 20,000 to 200,000 rpm or more, which, depending on the diameter of the burr, can provide surface speeds of the abrasive particles on the burr above or below 40 ft/sec. Auth claims that at surface speeds below 40 ft/sec the abrasive burr will remove hardened atherosclerotic material but will not damage normal elastic soft tissue of the vessel wall. Auth also admits that at surface speeds above 40 ft/sec the abrasive burr will remove both hardened and soft tissue. See, e.g., U.S. Pat. No. 4,990,134 at col. 3, lines 20–23. Unfortunately not all atherosclerotic plaques are hardened, calcified atherosclerotic plaques. Moreover, the mechanical properties of the soft plaques are very often quite close to the mechanical properties of the soft wall of the vessel. Thus, one cannot safely rely entirely on the differential cutting properties of such abrasive burrs to remove atherosclerotic material from an arterial wall, particularly where one is attempting to entirely remove all or almost all of the atherosclerotic material. See, e.g., *Atherectomy, A Physicians Guide*, (Strategic Business Development, Inc., 1990), pp. 89, 94–96. Furthermore, the Auth burr effectively blocks blood flow through the artery during the passage of the burr through the stenosis, thus limiting the amount of time of each pass across the stenosis to less than one minute (and perhaps as little as 10 seconds). See id. at pp. 95–96. Because the size of the particles removed by the Auth burr is very small (typically 5 microns or less), and because of the time limitations described above, in clinical practice, in order to remove a sufficient amount of tissue during each pass of the burr across the stenosis, the Auth burr is virtually always rotated at speeds of at least about 155,000 rpm. At such speeds a diamond dust covered burr with a diameter of 1.5 mm achieves a surface speed of 40 ft/sec, the very speed at which the differential cutting effect becomes limited, at best (i.e., the burr removes both hard and soft tissue).

The ability of diamond dust covered burrs to remove human soft tissue at high surface speeds (e.g., small diameter burrs rotated at about 200,000 rpm) has been known for some time and has been utilized in dentistry since at least the early 1980's to remove soft gum tissue (see, e.g., "Premier Two Striper ® Gingival Curettage" (Abrasive Technology, Inc. 1982); "Premier Two Striper ® Crown & Bridge Techniques" (Abrasive Technology, Inc. 1981); H. Gilmore, et. al, *Operative Dentistry* (C.V. Mosby Company 1982, 4th ed.), pp. 348–350; R. Tupac, et al., "A Comparison of Cord Gingival Displacement With the Gingitage Technique," *Journal of Prosthetic Dentistry*, (Nov. 1981, pp. 509–515).

Several problems have been recognized in use of the Auth-type of burr, however. First, although under some conditions the differential cutting properties of such burrs are effective to protect healthy tissue, in many circumstances the burr nevertheless can abrade at least a portion of the healthy tissue, creating a risk of perforation. This is particularly true at higher rotational speeds. A majority of atherosclerotic lesions are asymmetrical (i.e., the atherosclerotic plaque is thicker on one side of the artery than on the other). Moreover, pressure of the burr against the atherosclerotic plaque is achieved only by the use of a burr having a diameter slightly larger than the opening through the stenotic passageway. Thus, since the stenotic material will be entirely removed on the thinner side of an eccentric lesion before it will be removed on the other, thicker side of the lesion, during removal of the remaining thicker portion of the atherosclerotic plaque the burr necessarily will be engaging healthy tissue on the side which has been cleared—indeed, lateral pressure by such healthy tissue against the burr is required to keep the burr in contact with the remaining stenotic tissue on the opposite wall of the passageway. For stenotic lesions that are entirely on one side of an artery (a relatively frequent condition), this means that the healthy tissue across from the stenotic lesion will be exposed to and in contact with the abrasive burr for substantially the entire procedure. Moreover, pressure from that healthy tissue against the burr will be, in fact, the only pressure urging the burr against the atherosclerotic plaque. Under these conditions, a certain amount of damage to the healthy tissue is almost unavoidable, even though undesirable, and there is a clear risk of perforation. Thus, in clinical practice (balancing safety and residual stenosis), physicians rarely use a burr diameter of more than 2 mm, even on patients where the original diameter of the coronary artery lumen is estimated to be 3 mm. See, e.g., *Atherectomy, A Physicians Guide,* (Strategic Business Development, Inc., 1990), p. 96. These risks are enhanced at high rotational speeds where the differential cutting phenomenon is significantly diminished.

As indicated above, in clinical practice the opening of the stenosis of coronary arteries using the Auth-type burr is performed very fast and thus very large numbers of small particles of stenotic material (estimated to be 1,000,000 per cubic mm of stenotic material removed—see id. at p. 92) are released into the coronary artery within a very short period of time. Although individually the particles (typically in the range of 5 microns) can easily pass through the capillaries, when such large numbers of such particles are released within a very short period of time it is very possible that there is a risk that they may at least temporarily occlude the capillaries. This may explain the heart pain which is not infrequently experienced by patients immediately after the Auth-type burr is passed across the stenosis, as well as elevated levels of enzymes indicative of myocardial ischemia (such as CPK) which have been documented in some patients after the Auth-type burr procedure. See id. at p. 95. In a prior patent application of Applicant's, Ser. No. 07/967,765, filed Oct. 28, 1992, incorporated herein by reference (the "'765 application"), Shturman described a rotational atherectomy apparatus with a special guide wire that gives directional control over the position of the atherectomy device's abrasive burr within a body passageway, thereby providing a method for controlled removal of tissues from body passageways, such as atherosclerotic plaques from arteries. The Shturman rotational atherectomy apparatus, as with the Auth-type device, includes a rotatable abrasive burr carried at a distal end of a flexible, elongated drive shaft. The drive shaft in turn typically is disposed in a catheter having a central lumen, and is connected to means for rotating the drive shaft at high speeds. The special guide wire of the Shturman rotational atherectomy apparatus comprises a flexible, generally straight proximal portion, a flexible distal tip portion, and a flexible intermediate burr-positioning segment with a predetermined curved shape. This curved intermediate burr-positioning segment controls the lateral position of the burr within the body passageway and is, in fact, responsible for directional control over the rotational atherectomy device. The guide wire is sized so that its proximal end can be inserted into the distal end of the drive shaft lumen, permitting the drive shaft and burr to be advanced longitudinally over the guide wire to locate the burr along the predetermined shape of such intermediate burr-positioning segment, thereby selectively positioning the burr laterally away from the longitudinal axes of the proximal and distal portions of the guide wire.

The lateral position of the burr of this Shturman device within the body passageway is controlled by the degree of lateral deflection and the orientation of the curve of the intermediate burr-positioning segment of the guide wire. Thus, by advancing or retracting the drive shaft and burr with respect to the guide wire, the burr can be selectively located along the burr-positioning segment of the guide wire to selectively position the burr laterally of the axes of the proximal and distal portions of the guide wire. Guide wires having intermediate burr-positioning segments with different shapes can be used to control both the lateral position and the angular orientation of the burr, providing great flexibility in positioning the burr to remove unwanted tissue (such as an atherosclerotic plaque).

The Shturman apparatus described in the '765 application provides several distinct advantages over devices such as the Auth and Simpson atherectomy devices. With respect to Auth-type devices, there are a number of advantages to the Shturman apparatus:

1. It provides directional control over the removal of stenotic tissue, reducing the risk of damage to or perforation of the normal vascular wall;

2. It provides a small diameter burr-based instrument capable of opening stenoses in large diameter peripheral arteries (such as the femoral and iliac arteries) without resorting to entry through a cut-down on the femoral artery;

3. It does not completely occlude the blood flow through an artery during an atherectomy procedure, thus not limiting the time available to the physician to open the stenosis; and 4. It provides for slower, controlled release of particles of stenotic material into the capillaries over a longer period of time.

With respect to the Simpson-type atherectomy devices, the Shturman apparatus provides at least two additional advantages:

1. It is very flexible (compared to Simpson-type devices which typically have a rigid housing), permitting its use in small, more tortuous arteries: and 2. It provides the ability to remove hard, calcified stenotic tissue.

In another Shturman application Ser. No. 07/962,634, filed Oct. 16, 1992, incorporated herein by reference (the "'634 application"), Shturman described yet another device for directional rotational atherectomy where the lateral positioning of the abrasive burr is controlled not by a burr positioning segment of a guide wire, but by a specially designed positioning wire which also has a burr-positioning segment. This second Shturman device includes an elongated catheter having at least two lumens, and the guide wire and positioning wire are located inside these separate lumens. Distally of the catheter the positioning wire is slidably attached to the guide wire. Compared to the first-mentioned Shturman apparatus (the '765 application), this second Shturman device provides two significant additional advantages over the Auth-type atherectomy device:

1. It allows one to widely open even large coronary arteries to their large original diameter without significant residual stenosis using a single directional rotational atherectomy instrument rather than multiple instruments with successively larger diameter burrs (which often still leave significant residual stenosis);

2. It permits use of intravascular ultrasound imaging to image a cross-section of the stenotic area (including the thickness and composition of the atherosclerotic plaque), and the relative position of the abrasive burr with respect to the stenotic tissue. The intravascular ultrasound imaging permits monitoring of the removal of the stenotic tissue as it is being removed, thus further enhancing the safety of the procedure.

Both of the Shturman devices and the Auth device have several drawbacks due to the fact that a separately manufactured abrasive burr must be attached to (or near) the distal end of the flexible drive shaft. First, the connection between the burr and the drive shaft is critical, in that it must be secure against failure. This requirement therefore adds to the cost of producing the device.

Second, the size of the burr necessarily limits the ability of the device to be advanced into and through small diameter and/or tightly stenotic arteries.

Third, friction of the diamond dust covered burr against the stenotic tissue results in a frictional force. The torque applied to the rotating drive shaft due to this frictional force is generally proportional to the lever arm (or moment arm) of the frictional force, and thus is always larger for a drive shaft with a burr than for the same drive shaft without a burr since the diameter of the burr mounted on the drive shaft is always larger than the diameter of the drive shaft itself. Thus, it would be desirable to find a way to reduce the lever arm of the frictional force acting on the drive shaft, thereby reducing the torque acting on the drive shaft and thus reducing the risk of drive shaft failure.

SUMMARY OF THE INVENTION

The invention provides a directional rotational atherectomy device that eliminates the three above-described drawbacks. In one embodiment, the device comprises a rotational atherectomy device having a flexible, elongated drive shaft having a distal segment directly coated with an abrasive material to define an abrasive segment of the drive shaft. The drive shaft is advanced over a guide wire having a flexible, generally straight proximal portion, a flexible distal end portion, each such portion having a longitudinal axis, and a flexible intermediate positioning segment. The positioning segment has a predetermined curved shape such that when the abrasive segment is advanced over the guide wire to a position along the curved positioning segment, such curved positioning segment of the guide wire locates the abrasive segment of the drive shaft laterally away from one or both (proximal and distal) longitudinal axes of the guide wire.

In another embodiment, the device comprises an elongated catheter having at least two lumens. A guide wire is receivable in the first of the catheter lumens, and extends distally from the catheter. A flexible, elongated drive shaft is receivable in the second catheter lumen, and is longitudinally movable therein. The drive shaft includes a segment, near its distal end, which is coated with an abrasive material, thereby defining an abrasive segment of the drive shaft. A positioning wire is receivable in the drive shaft lumen. The positioning wire includes means for slidably securing its distal end about the guide wire distally of the distal end of the catheter so that the positioning wire can be moved proximally and distally with respect to the guide wire. The positioning wire also includes a distal positioning segment having a predetermined shape, the drive shaft being movable longitudinally with respect to the positioning wire to selectively locate the drive shaft's abrasive segment along the predetermined shape of the positioning segment of the positioning wire to selectively position the abrasive segment of the drive shaft laterally of the guide wire.

In either embodiment, the drive shaft is generally comprised of flexible helically wound multistrand wire coil. The abrasive material may be secured to the turns of the wire of the drive shaft coil by any suitable bonding material. The bonding material may be applied to the turns of the wire of the drive shaft coil so as to not only bond the abrasive material to the drive shaft but also to bond adjacent turns of the wire of the drive shaft coil to one another, thereby forming a generally nonflexible abrasive segment in the drive shaft. Alternately, the bonding material may be applied so as to not bond adjacent turns of the wire of the drive shaft coil to one another, thereby preserving the flexibility of the drive shaft throughout the abrasive segment. In yet another variation, bonding material may be applied to two or more short sub-segments of the abrasive segment so as to render each abrasive sub-segment generally inflexible while maintaining flexiblity between the sub-segments.

Usually the diameter of an abrasive segment of the drive shaft exceeds the diameter of the drive shaft coil itself by only the thickness of a circumferential layer of diamond particles (typically about 10–30 $\mu$m thick) and the thickness of a layer of bonding material which usually does not exceed about 5–10 $\mu$m. Thus, the overall diameter of the abrasive segment typically will be only about 30–80 $\mu$m larger than the diameter of the drive shaft coil itself.

The invention solves the above-identified drawbacks of the Auth and Shturman devices in that:

(1) the invention does not require a separately manufactured burr to be attached to the drive shaft, (2) the overall diameter of the abrasive segment for a given drive shaft can be made significantly smaller than an abrasive burr for the same diameter drive shaft, thereby allowing controlled treatment of extremely tight stenoses, and, (3) the likelihood of failure of the drive shaft due to excessive torque applied to the drive shaft is reduced since torque generated by frictional forces is always proportional to the radius of the abrasive segment, which is always smaller than the radius of the abrasive burr for the same diameter drive shaft.

BRIEF DESCRIPTION OF THE DRAWINGS

FIG. 7 is a view similar to FIG. 2, depicting the use of radio-opaque markers on the drive shaft, as well as the distal end of a thin, flexible sheath which covers most of the length of the drive shaft;

FIG. 8 is an enlarged view of a portion of an abrasive drive shaft (abrasive material not shown) of the invention, with turns of the wire of the drive shaft coil having two different pitches;

FIGS. 13-21 depict a sequence of steps in use of one embodiment of the; abrasive drive shaft atherectomy device of the invention in removing a stenosis in an artery—FIG. 13 is a partially broken away view of the abrasive drive shaft atherectomy device of the invention inserted into an artery having a stenosis to be removed, the distal positioning segment of the positioning wire being located in the most narrow portion of the stenosis;

FIG. 14 is a partially broken away view similar to FIG. 13 showing the device with the catheter withdrawn proximally in relation to the stenosis and the positioning wire, the distal positioning segment of the positioning wire having partially regained its predetermined shape, thus positioning the abrasive segment against the atherosclerotic plaque;

FIG. 15 is a view similar to FIGS. 13 and 14, with the abrasive segment having removed a portion of the atherosclerotic plaque;

FIG. 16 is a view similar to FIGS. 13-15 with the catheter, positioning wire, and drive shaft (with its abrasive segment) being withdrawn;

FIG. 17 is a view similar to FIG. 16, showing all components of the abrasive drive shaft atherectomy device (except for the guide wire) having been withdrawn;

FIG. 18 is a view similar to FIG. 13, with the abrasive drive shaft atherectomy device having been reinserted with a different positioning wire for continued removal of the stenosis;

FIG. 19 is a view similar to FIG. 14 but with an alternate positioning wire (with greater lateral deflection), its distal positioning segment being freed from the catheter to urge the abrasive segment further laterally toward the stenosis;

FIG. 20 is a view similar to FIG. 19, showing continued removal of the stenosis;

FIG. 21 shows the abrasive drive shaft atherectomy device of the invention being withdrawn;

FIG. 22 is a view similar to FIG. 14 showing use of the abrasive drive shaft atherectomy device of the invention in removing a stenosis occurring at the ostium of a branch of an artery (an osteal stenotic lesion), the guide wire extending from the main artery into the branch artery;

FIG. 23 is a view similar to FIG. 22, showing an alternate position of the abrasive drive shaft atherectomy device in removing such an osteal stenotic lesion, the guide wire being located in the main artery only (i.e., not extending into the branch artery), and the positioning wire also having a distal positioning segment with a different shape than the positioning wire shown in FIG. 22;

FIG. 24 is a partially broken away view of the proximal and distal end portions of the abrasive drive shaft atherectomy device of the invention, similar to FIG. 1, with the addition of an intravascular ultrasound imaging catheter positioned over the guide wire;

FIG. 25 depicts the abrasive drive shaft atherectomy device of the invention with such an intravascular ultrasound imaging catheter being positioned within an artery adjacent to a stenotic segment;

FIG. 25A is a cross-sectional view of FIG. 25, taken along line 25A—25A thereof, and FIG. 25B represents the ultrasound image generated by the intravascular ultrasound imaging catheter at this position;

FIG. 26 illustrates a positioning wire having a radio-opaque marker (coating) on its distal positioning segment;

FIG. 27 illustrates the abrasive drive shaft atherectomy device of the invention with a radio-opaque marker located near the distal end of the catheter;

FIGS. 28-34 illustrate several configurations of the positioning wire;

FIGS. 35-37 illustrate several possible configurations for the distal end of the positioning wire;

FIGS. 38-40 illustrate alternate embodiments for means connecting the distal end of the positioning wire slidably to the guide wire, and FIGS. 38A, 39A, and 40A are cross-sectional views, respectively, of FIGS. 38, 39, and 40;

FIG. 41 is a cross-sectional view of a guide wire having a stop located proximally to the distal end of the guide wire;

FIGS. 42-43 illustrate use of the abrasive drive shaft atherectomy device of the invention with the guide wire of FIG. 41, the advancement of the positioning wire against the stop causing lateral deflection of the abrasive segment;

FIG. 44 illustrates the use of braiding reinforcement in the catheter;

FIG. 44A is a cross-sectional view of FIG. 44, taken along line 44A—44A.

FIGS. 46-51 depict a sequence of steps in use of this alternate embodiment of the invention in removing a stenosis in an artery—FIG. 46 is a partially broken away view of the rotational atherectomy device of the invention inserted into an artery having a stenosis to be removed, the abrasive segment of the drive shaft being located at the top of the positioning segment of the guide wire, and just proximally to and on the side of the stenosis;

FIG. 47 is a view similar to FIG. 46 with both the guide wire and the abrasive segment advanced forward partially across the stenosis, the abrasive segment having removed a proximal portion of an inner layer of the atherosclerotic plaque;

FIG. 48 is a view similar to FIGS. 46-47 with the entire inner layer of the atherosclerotic plaque having been removed;

FIG. 49 is a view similar to FIG. 48, with the drive shaft and catheter being withdrawn;

FIG. 50 is a view similar to FIG. 49, with a new rotational atherectomy device with a larger diameter drive shaft (and, therefore, larger diameter abrasive segment) having been inserted for continued removal of the stenosis;

FIG. 51 is a view similar to FIG. 50 with both the guide wire and the larger abrasive segment advanced forward across the stenosis, the abrasive segment having removed almost all of the outer layer of the atherosclerotic plaque;

FIG. 52 illustrates a guide wire of the device of the invention having a predetermined lateral deflection of the positioning segment;

FIG. 53 illustrates a guide wire having a radio-opaque marker (coating) on its positioning segment;

FIG. 54 is a view similar to FIG. 52, illustrating a guide wire of the invention having a different curved shape; and FIG. 55 is another view similar to FIG. 52, illustrating a guide wire of the invention having another curved shape.

BEST MODE FOR CARRYING OUT THE INVENTION

Although the drawings illustrate use of the abrasive drive shaft device of the invention in connection with removal of atherosclerotic plaques in arteries, the device is usable in other capacities, wherever tissue or obstructions are desired to be removed from a body passageways, cavities, or any organ or organ system of the body.

Figure 1:
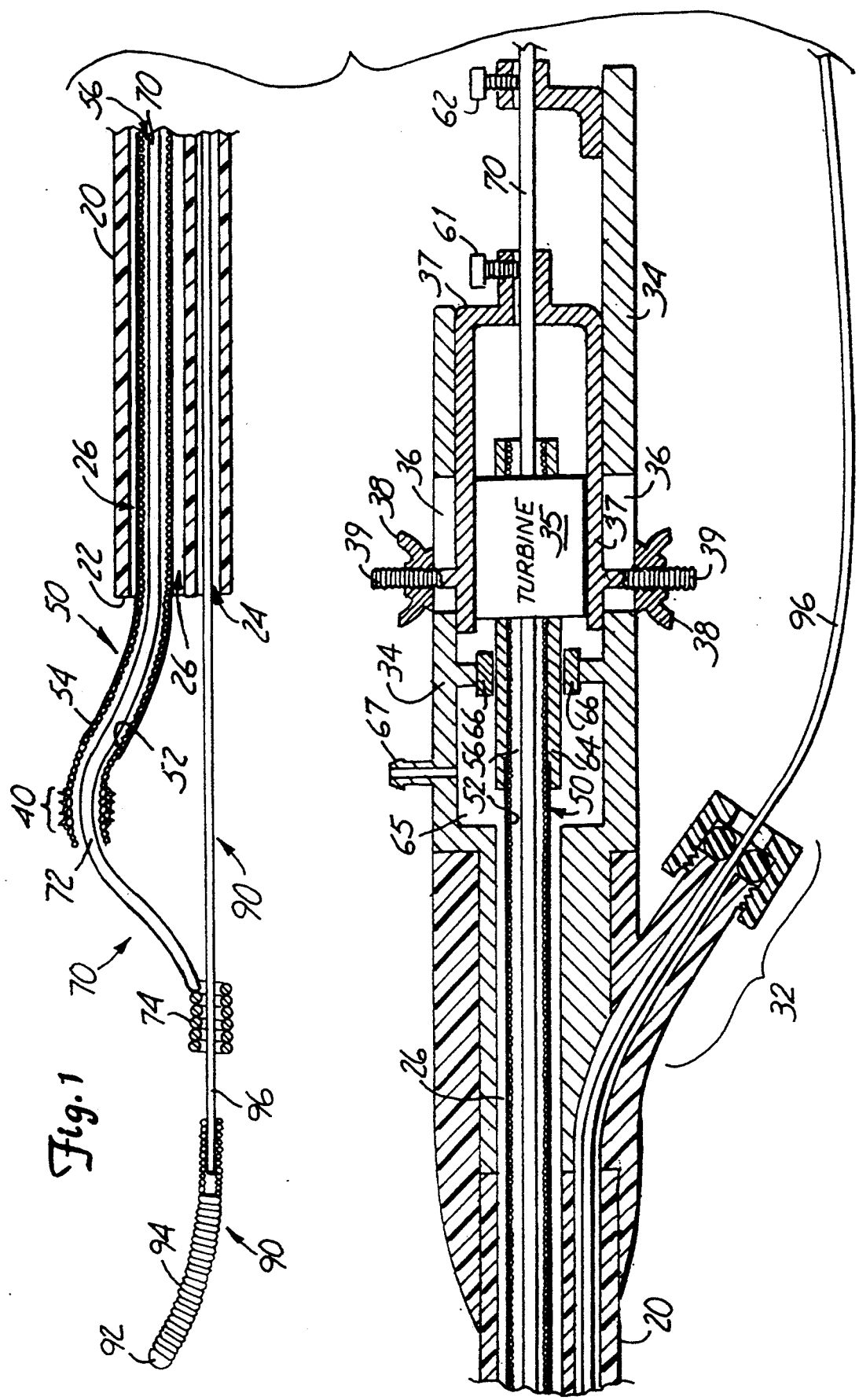
FIG. 1 is a partially broken away view of the proximal and distal end portions of one embodiment of the abrasive drive shaft atherectomy device of the invention, shown somewhat schematically and in cross-section.

FIG. 1 illustrates the principal components of one embodiment of the device. An elongated catheter 20 with a distal end 22 includes at least a pair of lumens 24 and 26. The first of these is sized to receive a conventional guide wire 90 having an elongated shaft 96 and a conventional helically wound distal tip portion 94, terminating in a rounded tip 92.

In the other lumen 26 of the catheter 20, a multistrand helically wound flexible drive shaft 50 is disposed. The shaft 50 is generally comprised of a helical coil 52, at least the intermediate portion of which is preferably encased in a thin, flexible Teflon ® sheath 54. A thin layer of abrasive material is deposited on a portion of the drive shaft 50 near the shaft's distal end, defining an abrasive segment 40.

A positioning wire 70 is disposed in the lumen 56 of the flexible drive shaft 50. The positioning wire 70 includes a distal end 74 which is slidably secured about the shaft 96 of the guide wire 90, and a distal positioning segment 72 which has a predetermined shape. The shape illustrated in FIG. 1 is such that the abrasive segment 40 is positioned laterally away from the guide wire 90.

The proximal portion of the catheter 20, as shown in the lower half of FIG. 1, is secured to a housing 34. Operatively attached to the housing 34 is a fitting 32 through which the guide wire shaft 96 can be advanced and withdrawn. A turbine 35 (or equivalent source for rotational motion) is secured to a turbine mount 37 slidably received in the housing 34. Relative longitudinal sliding movement of the turbine mount 37 with respect to the housing 34 is permitted, and, when it is desired to lock the longitudinal position of the turbine 35 and turbine mount 37 with respect to the housing 34, wing nuts 38 can be tightened on threaded bolts 39 (which extend from the turbine mount 37 through slots 36 in the housing 34). Alternately, equivalent means may be used to prevent relative longitudinal movement of the turbine and turbine mount with respect to the housing.

The turbine 35 is connected by way of turbine link 64 to the flexible drive shaft 50. A conventional seal 66 may be provided against the outer surface of the turbine link 64, preventing fluid from escaping from the cavity 65 while permitting rotational and longitudinal movement of the flexible drive shaft 50 and the turbine link 64. A side port 67 may be provided to permit infusion of lubricating fluid (saline or glucose solutions and the like) or radio-opaque contrast solutions into the cavity 65 and the second lumen 26 of the catheter 20. The side port 67 could also be connected to a vacuum source for aspiration of fluid through the catheter's second lumen 26.

Set screws 61 and 62 are provided to selectively permit or prevent relative longitudinal movement of the positioning wire 70 with respect to the turbine mount 37 and with respect to the housing 34. Thus, if the set screw 62 is loosened while the screw 61 is tightened against the positioning wire, the positioning wire 70 and the flexible drive shaft 50 (which is rigidly connected to the turbine 35 and hence to the turbine mount 37) can be advanced and retracted as a unit with respect to the catheter 20 and the housing 34. Alternately, loosening of set screw 61 and tightening of set screw 62 will permit relative longitudinal movement of the flexible drive shaft 50 and its abrasive segment 40 with respect to the positioning wire 70 allowing one to locate the abrasive segment at an appropriate place on the positioning segment of the positioning wire 70. When both set screws 61 and 62 are loosened then obviously one can move the positioning wire longitudinally relative to both the catheter 20 and the flexible drive shaft.

Although the means for securing the positioning wire 70, the turbine mount 37 and the housing 34 with respect to one another are illustrated in the drawing as being accomplished by use of wing nuts 38 and set screws 61 and 62, it will be appreciated that other conventional means or mechanisms (such as cam friction fittings, and the like) may easily be employed. Moreover, the connection of the proximal end of the catheter 20 to the housing 34, as well as the side port 67 and guide wire fitting 32 are shown somewhat schematically—any of a variety of conventional fittings that are readily commercially available or adaptable for this purpose may easily be employed. Furthermore, fitting 32 may be provided with an additional port (or equivalent means) for infusing flushing fluid into the first lumen 24 of the catheter 20.

Figure 2:
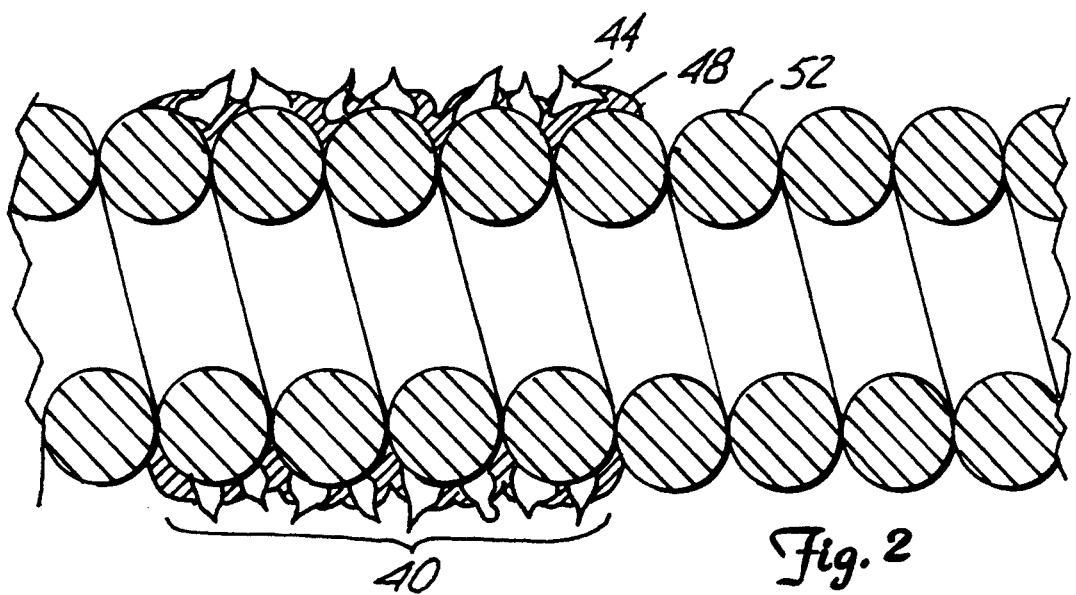
FIG. 2 is an enlarged, broken-away view in cross-section of the abrasive drive shaft of the invention, with abrasive material shown somewhat schematically attached to the turns of the wire of the drive shaft coil, the abrasive material being attached in such a fashion that adjacent turns of the wire of the drive shaft coil are secured to one another.

FIGS. 2–10 illustrate in enlarged, somewhat schematic fashion several alternate configurations for coating the abrasive material on the abrasive segment of the drive shaft. FIG. 2 shows that the drive shaft itself is generally comprised of flexible helically wound multistrand wire coil. Abrasive particles 44 are secured to the turns or windings 52 of the drive shaft coil by a bonding material 48. The method for attaching the abrasive particles 44 to the surface of a the drive shaft may employ any of several well known techniques, such as conventional electroplating, fusion technologies (see, e.g., U.S. Pat. No. 4,018,576), brazing, adhesives and the like. The abrasive particles 44 themselves may be of any suitable composition, such as diamond powder, fused silica, titanium nitride, tungsten carbide, aluminum oxide, boron carbide, or other ceramic materials. Preferably they are comprised of diamond chips (or diamond dust particles). Abrasive materials of these types have been used in a variety of medical/dental applications for years and are commercially available. The attachment of abrasive particles to the abrasive segment of the drive shaft is also commercially available from companies such as Abrasive Technologies, Inc. of Westerville, Ohio.

Figure 3:
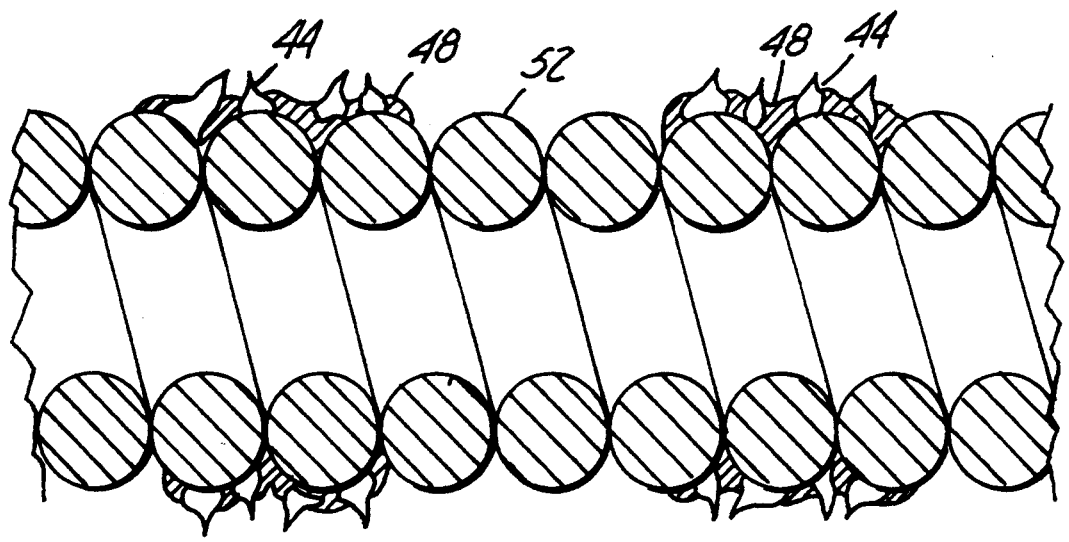
FIG. 3 is a view, similar to FIG. 2, of an alternate embodiment where abrasive material is attached in spaced sub-segments, i.e., with an intermediate portion of the abrasive segment being free of abrasive material, thereby providing flexibility to the abrasive segment.

In FIG. 2 the bonding material 48 is applied over the entire outer surface of the abrasive segment 40 of the drive shaft, thereby not only bonding the abrasive particles 44 to the turns 52 of the wire of the drive shaft coil, but also securing adjacent turns 52 of the wire of the drive shaft coil to one another, creating a short relatively rigid segment in the otherwise flexible drive shaft. In FIG. 3 the bonding material 48 has been applied to the drive shaft in short circumferential cylinders or rings, thus creating an overall abrasive segment in the flexible drive shaft that is composed of several short abrasive sub-segments; each individual sub-segment is relatively rigid, but the un-bonded space between the sub-segments provides a degree of flexibility to the overall abrasive segment.

Figure 4:
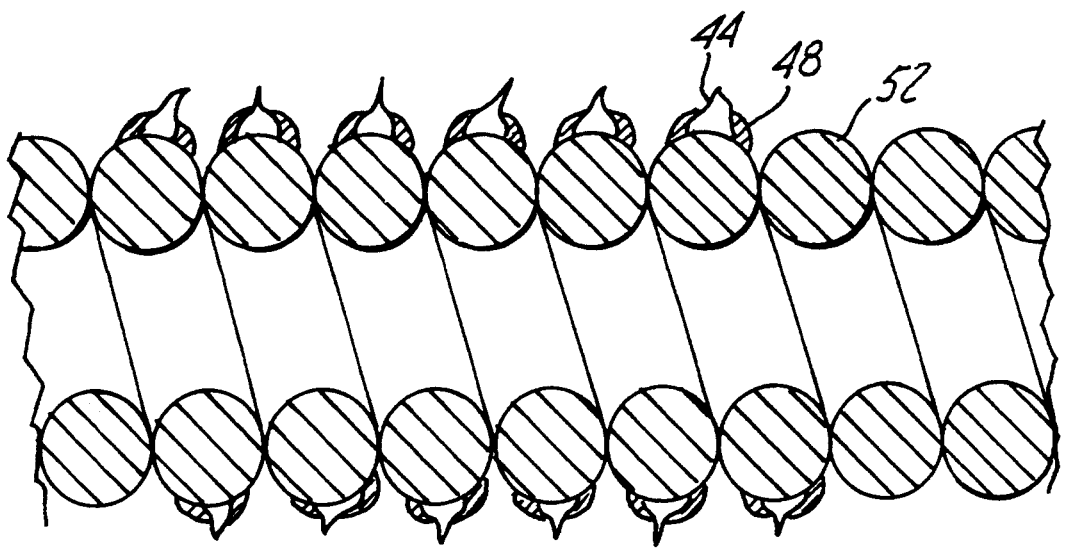
FIG. 4 shows another embodiment with abrasive material attached to the turns of the wire of the drive shaft coil without attaching adjacent turns of the wire of the drive shaft coil to one another.

In FIG. 4, the bonding material 48 has been applied to the turns of the wire of the drive shaft coil in a fashion that effectively secures the abrasive particles 44 to the wire turns 52 of the drive shaft coil without securing the wire turns 52 of the drive shaft coil to one another. This provides the abrasive segment of the drive shaft with essentially the same degree of flexibility as the rest of the drive shaft.

Figure 5:
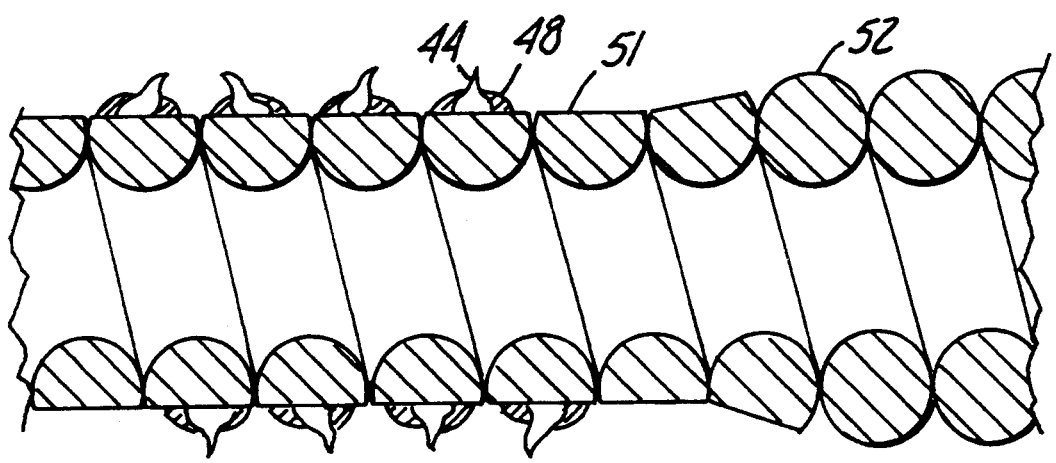
FIG. 5 shows an embodiment similar to FIG. 4, but with the turns of the wire of the abrasive segment of the drive shaft coil having been machined flat before attachment of the abrasive material.
Figure 6:
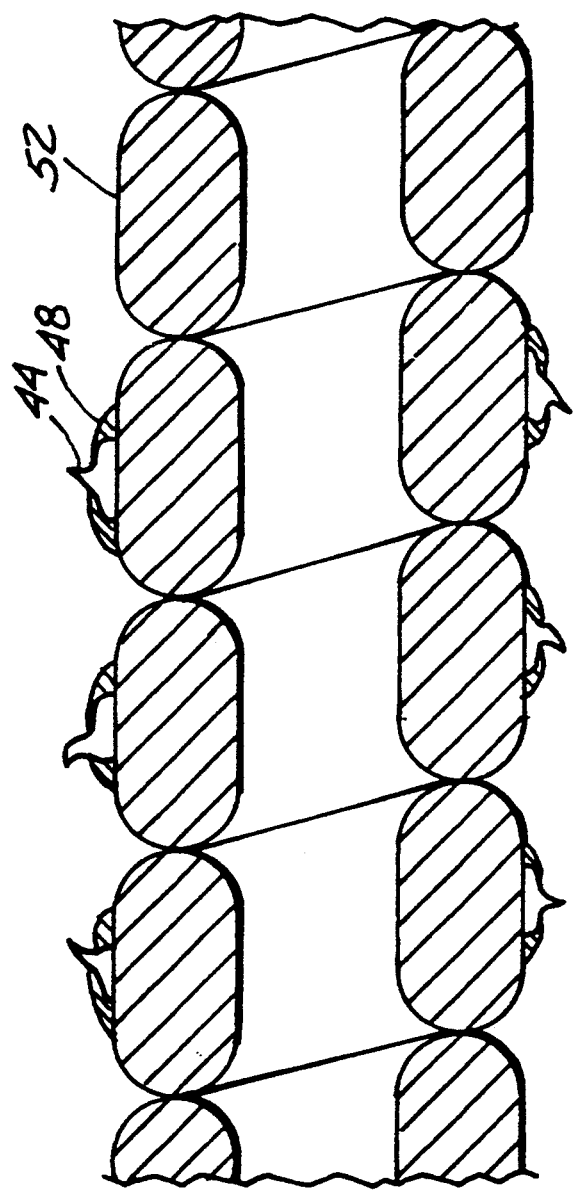
FIG. 6 shows an embodiment similar to FIG. 4, but with generally flat wire being used for the drive shaft.

FIG. 5 illustrates an embodiment similar to FIG. 4 but with the outer surface of the abrasive segment having been machined or milled to present a generally flat, smooth outer surface 51 for bonding of the abrasive particles 44. Again, the bonding material 48 has been applied so as not to bond adjacent turns of the wire of the drive shaft coil to one another. In FIG. 6, generally flat wire (i.e., rectangular wire with rounded corners) has been used in manufacturing the drive shaft, thereby providing a similar flat outer surface to which abrasive particles 44 may be attached. Such rectangular/flat wire can be of any suitable dimensions. For example, wire having a cross-sectional height of about 0.002–0.008 inches, and a width of up to about three to five times the height may be utilized. Stainless steel wire of this type is commercially available from various sources, including the Wire Division of MicroDyne Technologies (New Britain, Conn.).

FIG. 7 illustrates the use of radio-opaque rings or collars 106 and 107, respectively just distal to and just proximal to the abrasive segment 40, for assistance in imaging the location of the abrasive segment. The TEFLON ® (or other low-friction material) sheath 54 covering substantially the entire portion of the drive shaft proximal to the abrasive segment is also illustrated in FIG. 7.

Figure 8A:
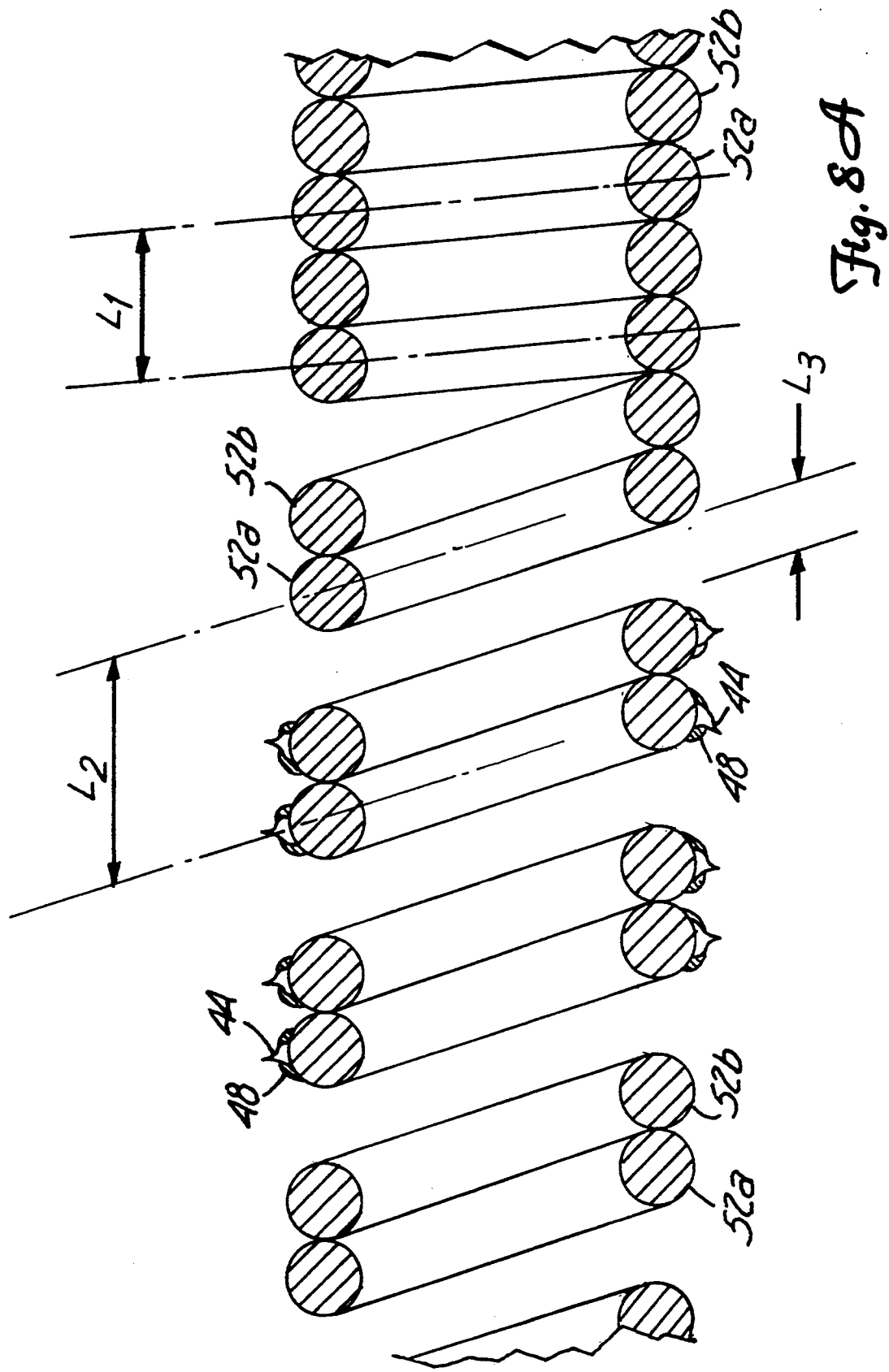
FIG. 8A is a longitudinal cross sectional view of FIG. 8, differing from FIG. 8 in that abrasive material (shown somewhat schematically) is depicted on some of the turns of the wire of the drive shaft coil.

FIG. 8 illustrates a bi-filar drive shaft 50 of the invention being comprised of a pair of helically wound wires 52a and 52b. For clarity, the abrasive material bonded to the turns of the drive shaft 50 is not shown in FIG. 8. FIG. 8A is a longitudinal cross sectional view of FIG. 8, differing from FIG. 8 in that abrasive material (shown somewhat schematically) is depicted on the turns of the wire of the abrasive segment of the drive shaft. A proximal portion of the drive shaft helical coil 50 has a pitch $L_1$ and a distal portion has a larger pitch $L_2$ with gaps $L_3$ between adjacent bi-filar turns of the drive shaft coil. The gaps provide for greater lateral flexibility of the distal portion of the drive shaft 50. Thus, the transition from pitch $L_1$ to pitch $L_2$ typically would occur near the distal end of the drive shaft at a point where greater flexibility is desired, usually several inches proximal to the distal end of the drive shaft, and at least just proximal to the portion of the drive shaft which will be located over the positioning segment of the positioning wire when the drive shaft is maximally advanced distally over the positioning wire. As illustrated in FIG. 8A, the gaps also make it easier to bond abrasive material to the turns of the drive shaft 50 without bonding successive turns to one another, thereby preserving lateral flexibility of the abrasive segment of the drive shaft.

Figure 9:
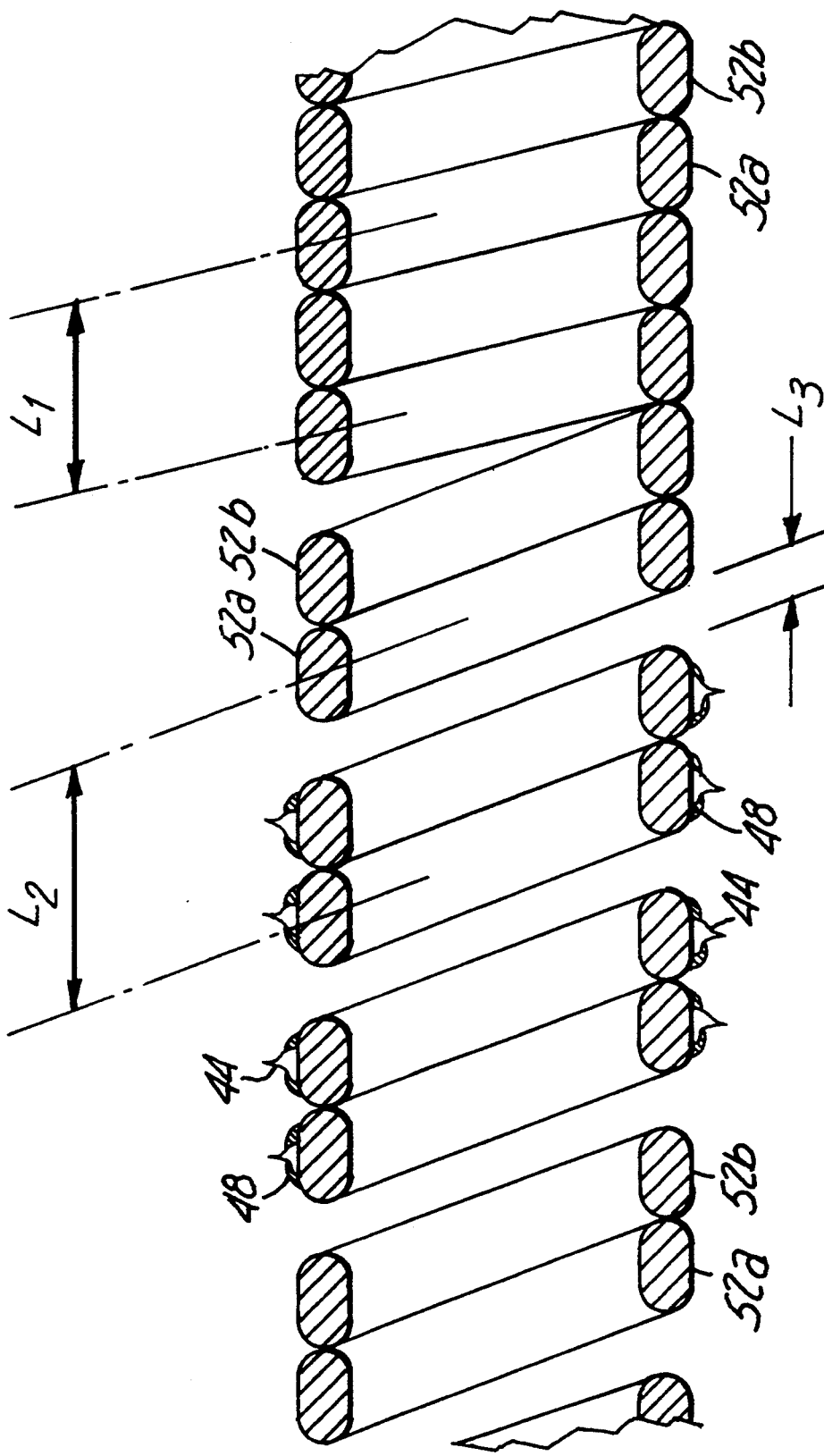
FIG. 9 is a view, similar to FIG. 8A, of a slightly modified embodiment utilizing generally flat wire.

FIG. 9 is a view similar to FIG. 8A, depicting a drive shaft 50 comprised of generally flat wire. Although, for the sake of clarity in the drawings, FIGS. 8, 8A and 9 all depict bi-filar drive shafts, in practice tri-filar drive shafts may be preferred over bi-filar drive shafts, but the principles illustrated in FIGS. 8–9 are equally applicable regardless of the number of wire strands making up the drive shaft.

Figure 10:
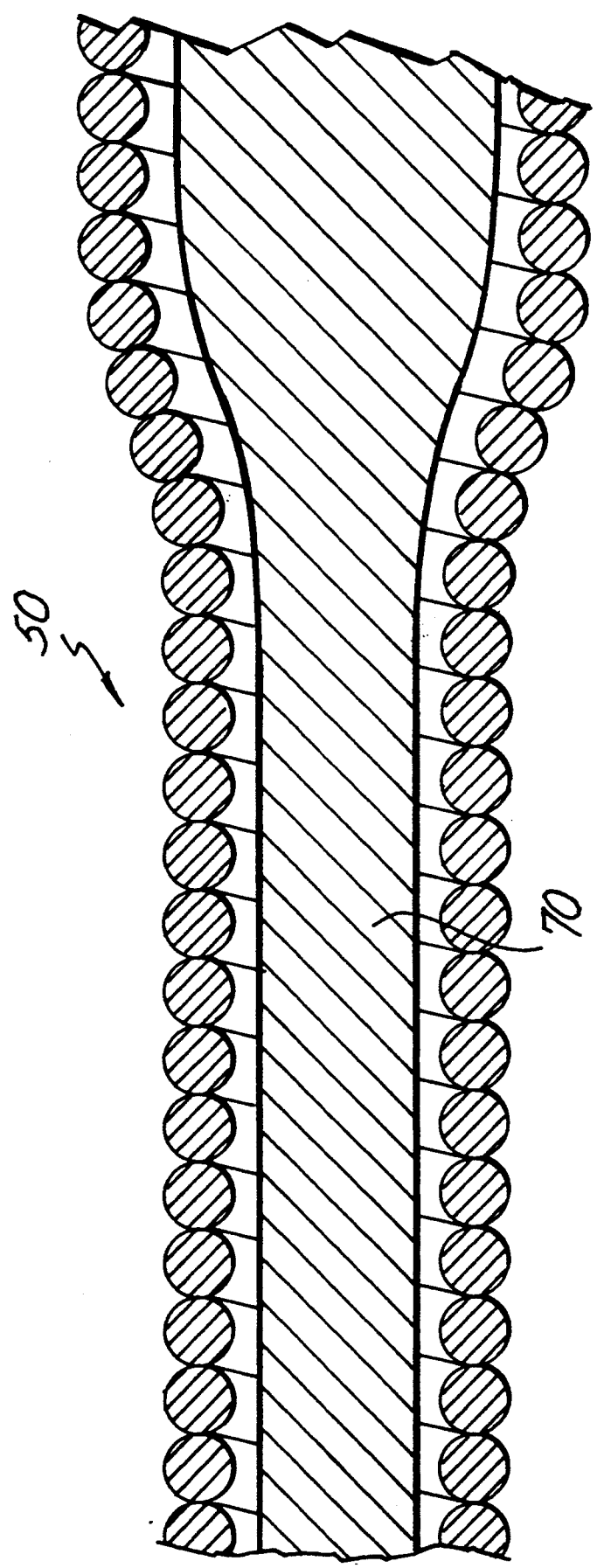
FIG. 10 is a longitudinal cross-sectional view of an intermediate portion of an embodiment of the drive shaft and positioning wire of the invention wherein the diameters of the drive shaft and positioning wire decrease distally.

FIG. 10 illustrates an embodiment of the invention where the positioning wire 70 and the drive shaft 50 decrease in diameter from a larger diameter proximal section to a smaller diameter distal section. The smaller diameter distal sections of the positioning wire 70 and the drive shaft 50 allow the distal portion of the atherectomy device of the invention to assume a lower profile and make the distal portion of the device more flexible, a characteristic which is desirable for the portion of the device that is designed to be located in narrow and tortuous arteries, e.g., the coronary arteries. The larger diameter proximal section has greater stiffness, giving better pushability and torque control throughout most of the length of the device. Desirably the transition from the larger diameter section to the smaller diameter section is located so that the entire section of the drive shaft intended to enter the coronary artery is of the smaller diameter. Typically this will be approximately 4–8" from the distal end of the drive shaft.

Figure 10A:
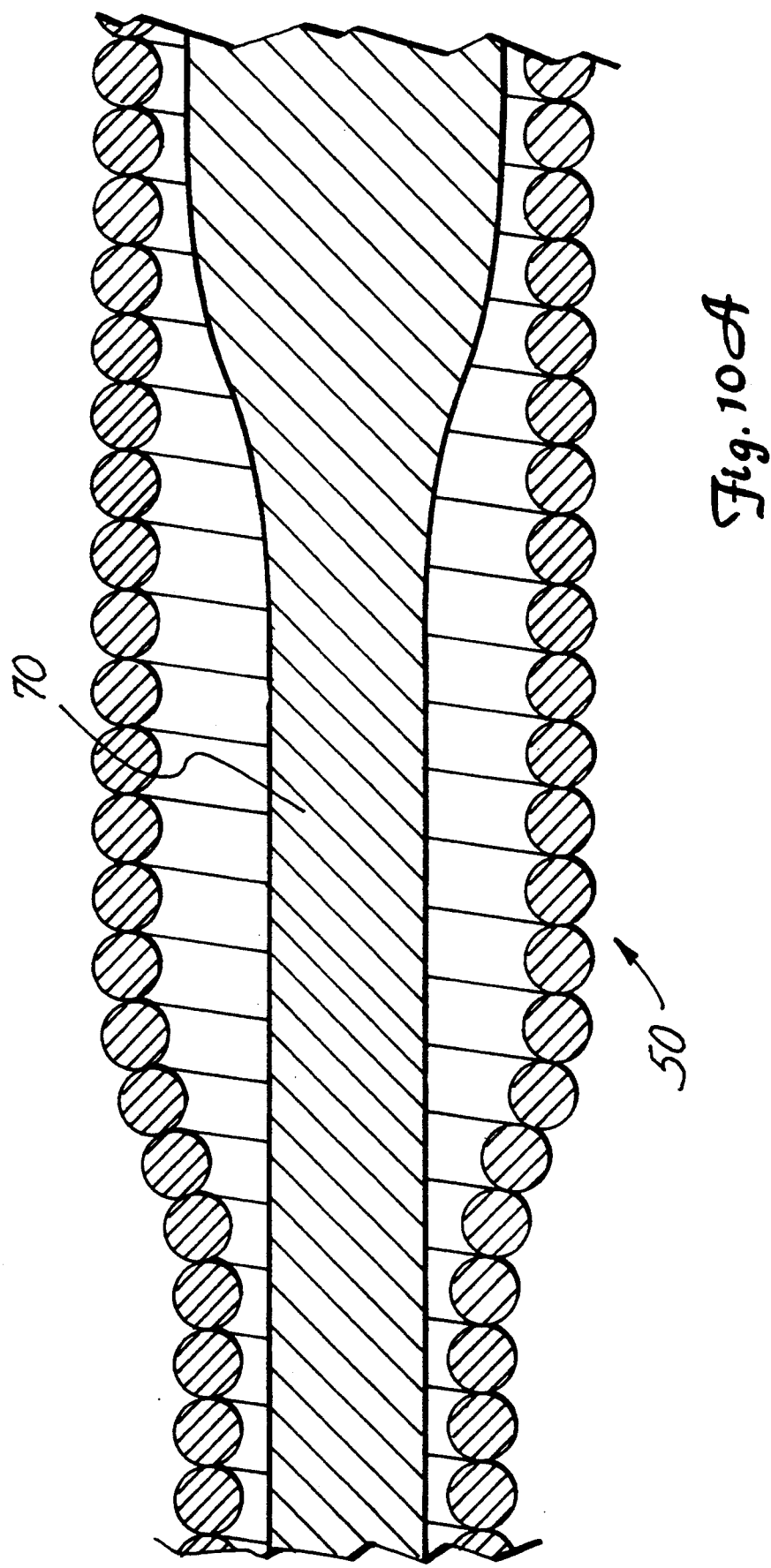
FIG. 10A is a view similar to FIG. 10 with the drive shaft having been moved distally with respect to the positioning wire.

FIG. 10A illustrates the fact that, despite this change in diameters of the positioning wire and the drive shaft, the drive shaft 50 can advanced and retracted with respect to the positioning wire 70—in FIG. 10A the drive shaft 50 has been advanced distally with respect to the positioning wire 70, and can easily be again withdrawn proximally the corresponding distance.

It will be appreciated that the representations in FIGS. 2–10 are somewhat schematic. In many of the views the abrasive particles 44 are shown as being attached in neat rows centered along the turns of the drive shaft. Depending on the method of applying the abrasive particles, the particles more likely will be distributed somewhat randomly over the abrasive segment (or wire turns) of the drive shaft. Moreover, the relative size of the abrasive particles in relation to the diameter of the wire of the drive shaft coil may vary from one application to another. In a typical application round wire having a diameter of about 75–125 μm may be wound into a drive shaft coil having an overall outer diameter of about 0.3–1.5 mm, and abrasive particles in the range of about 5 μm to about 30 μm are secured to the drive shaft with a bonding material having a thickness of from about 3 μm to about 15 μm (i.e., that portion of the bonding material which may be located between the particles and the drive shaft coil wire). Thus, the effective "thickness" of the abrasive material, including the bonding material, may be in the range of about 8 μm to about 45 μm, and preferably in the range of about 15 μm to about 35 μm.

Figure 11:
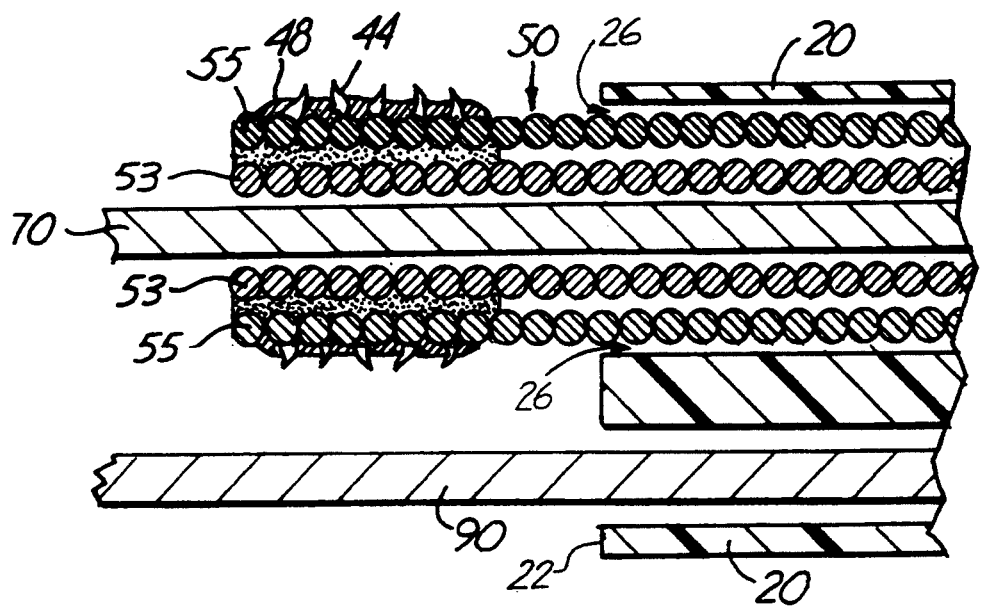
FIGS. 11-12 illustrate the use of a two-layer helically wound flexible abrasive drive shaft.
Figure 12:
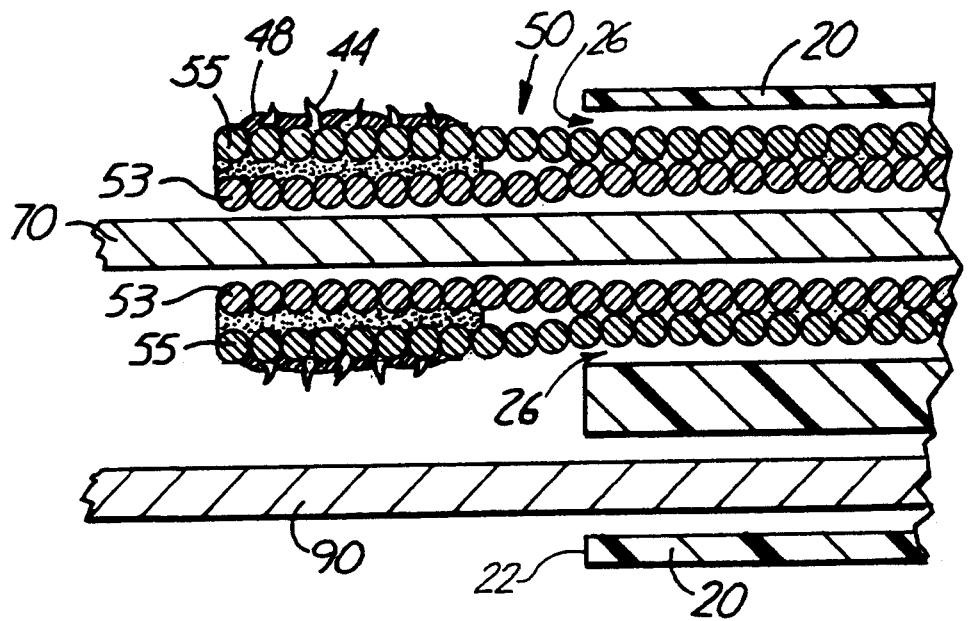

FIGS. 11 and 12 depict the use of a two-layer helically wound flexible drive shaft. In this embodiment, a pair of multi-strand coils 53 and 55 is disposed co-axially—one of them is wound counterclockwise, and the other is wound clockwise. Thus, viewing the drive shaft from its distal end, when it is rotated in the direction of the winding of the outer coil 55, torque on that coil will tend to decrease its diameter, while torque on the inner coil 53 will tend to increase its diameter. Thus, the opposing forces of the two coils against one another, as depicted in FIG. 49, will result in there being a slight increase in the gap between the inner wall of the catheter lumen 26 and the outer coil 55, as well as a slight increase in the gap between the outer surface of the positioning wire 70 and the inner surface of the inner coil 53. This will not only diminish the friction of the flexible drive shaft against the catheter lumen and the positioning wire, but will also decrease the risk of the flexible drive shaft either unwinding in the artery or locking onto the positioning wire. For applications in very small arteries, it may not be practical to use a two layer flexible drive shaft because of the inherent increase in diameter caused by the second layer.

The single layer multistrand helically wound flexible coil 52 and the two-layer flexible drive shaft described above are preferably made from stainless steel wire. Coils of this type are generally commercially available.

FIGS. 13–15 illustrate the operation and function of the abrasive drive shaft device of the invention in removing an atherosclerotic lesion or atheroma 12 from an artery 10. As indicated above, the device of the invention is particularly useful in removing asymmetrical stenotic lesions, such as the one illustrated in FIGS. 13–21. Although the device will work just as well with symmetrical stenotic lesions or only mildly asymmetrical stenotic lesions, the advantages of the invention are best illustrated with respect to an atherosclerotic lesion that is located predominantly on one side of the arterial wall 10.

Commercially available angioplasty equipment (e.g., arterial puncture needles, arterial dilators, sheath introducers and guide catheters) and routine angioplasty techniques are used to appropriately position the abrasive drive shaft device in the arteries of interest.

In FIG. 13, the guide wire 90 has been advanced through the artery to a position where its distal tip 92 is located distally of the stenosis. The catheter 20, including the positioning wire 70 and the flexible drive shaft 50 with its abrasive segment 40, has been advanced over the shaft 96 of the guide wire 90 to a position locating the abrasive segment 40 adjacent to the stenotic lesion 12. Note that during advancement of the catheter 20 through the artery, the catheter 20 has been advanced over a substantial portion (typically about the proximal one-half) of the distal positioning segment 72 of the positioning wire 70 and almost all of the length of the distal portion of the flexible drive shaft. This temporarily straightens (not completely, but substantially) the distal positioning segment 72 of the positioning wire 70 (which preferably is made of a shape-memory alloy such as nitinol), bringing the abrasive segment 40 to a lateral position close to the guide wire 90 with the positioning wire 70 almost parallel to the guide wire 90, and thereby giving the entire device a very low profile. Such a low profile of the distal end of the abrasive drive shaft device will enable the device to be advanced even into an area of very tight arterial stenosis.

In FIG. 14, the catheter 20 has been withdrawn with respect to the distal positioning segment 72 of the positioning wire 70, freeing the positioning segment 72 from the confines of the catheter 20, and allowing it to at least partially regain its predetermined shape. Since the abrasive segment 40, being positioned on the distal positioning segment 72, is engaged against the atherosclerotic lesion 12, the distal positioning segment 72 has not entirely regained its predetermined shape in FIG. 14, being limited by the presence of the atherosclerotic plaque. In FIG. 14, the abrasive segment 40 has been positioned at the crown of the positioning segment 72 of the positioning wire 70, putting the lateral surface of the abrasive segment 40 in direct contact with the atherosclerotic plaque 12.

At this point, the positioning wire 70, the catheter 20 and the flexible drive shaft 50 (with its abrasive segment 40) can be advanced distally and retracted proximally as a unit while the drive shaft is being rotated at relatively high speed (typically in the range of about 30,000 RPM to about 600,000 RPM, or even more, depending only on the physical dimensions and capabilities of the turbine/motor and flexible drive shaft) to selectively remove a portion of the stenotic lesion 12.

In FIG. 15, a portion of the stenotic lesion 12 has been removed, and the distal positioning segment 72 of the positioning wire 70 has now entirely regained its predetermined shape. Thus, at this point there is no significant further pressure of the abrasive segment 40 against the atherosclerotic lesion 12.

FIGS. 16–18 depict the successive removal of the abrasive drive shaft device (except for the guide wire) and replacement of the positioning wire 70 with a different positioning wire 70' having a distal positioning segment with a different shape which offers greater lateral deflection. Replacement of the positioning wire 70 can easily be accomplished by:

(1) withdrawing, if necessary, a substantial portion (typically the proximal half) of the positioning segment of the positioning wire 70, along with that portion of the drive shaft immediately proximal to the abrasive segment, into the catheter 20;

(2) withdrawing the positioning wire 70, together with the flexible drive shaft 50, and the catheter 20, out of the patient's body and further proximally off the proximal end of the guide wire 90;

(3) removing the positioning wire 70 from the central lumen 56 of the flexible drive shaft 50 by pulling it distally therefrom;

(4) inserting the new positioning wire 70' into the lumen 56 of the flexible drive shaft 50 by inserting the proximal end of the positioning wire 70' into the distal end of the drive shaft 50;

(5) again advancing the catheter 20 over the proximal portion of the positioning segment of the positioning wire and almost the full length of the drive shaft to again bring the abrasive segment 40 to a lateral position close to the guide wire, so that the distal end of the device again assumes a very low profile to facilitate its introduction back into the artery; and (6) advancing the positioning wire 70', the drive shaft 50 with its abrasive segment 40 and catheter 20 as a unit over the guide wire 90 to the position illustrated in FIG. 18 with the abrasive segment 40 again positioned adjacent to the atherosclerotic lesion 12.

Once in this position, the catheter can again be withdrawn with respect to the positioning wire 70', thus allowing the distal positioning segment 72' of the positioning wire 70' to again at least partially regain its predetermined shape, as illustrated in FIG. 19, thereby moving the abrasive segment laterally away from the guide wire and up against the atherosclerotic lesion 12. More of the atherosclerotic lesion 12 can then be removed, as illustrated in FIG. 20, until the distal positioning segment 72' has again fully regained its predetermined shape. When a sufficient amount of the lesion 12 has been removed, if necessary, the positioning segment 72' can again be withdrawn into the catheter 20 (or, equivalently, the catheter advanced over the positioning segment) to again draw the abrasive segment close to the guide wire 90, and the entire device, including the guide wire, can be withdrawn, as shown in FIG. 21.

As can be seen from the above discussion in reference to the drawings, during the entire procedure the abrasive segment 40 never need come into contact with the wall 10 of the artery across from the atherosclerotic lesion 12. Rather, the device provides directional control over the lateral location of the abrasive segment within the artery, permitting contact of the abrasive segment substantially only with stenotic tissue.

Lumens of a very large arteries can be re-opened to their original diameter (e.g., 5–7 mm in the iliac and femoral arteries) with use of a comparatively small diameter abrasive segment (e.g., about 1 mm in diameter or less), a capability not practically possible with the Auth-type device, which usually requires performing a cut-down on the common femoral artery in order to introduce the larger abrasive burrs (e.g., over 3 or 4 mm in diameter) of the Auth-type device. In some cases this would be entirely impossible, as the normal diameter of the artery through which the drive shaft with its abrasive burr preferably is introduced may only be, e.g., 3–4 mm or less. An example of this would be using the brachial artery approach (having a diameter of about 3–4 mm or less) to reach the iliac or femoral artery (having a diameter of 5–7 mm). Moreover, the abrasive drive shaft device of the invention designed for opening such large arteries may be introduced through arteries having an inner diameter as small as 2 mm or even less, a capability not practically possible even with the Shturman devices described in the '765 and '634 applications.

FIGS. 22 and 23 illustrate additional capability of the invention in gaining access to treat atherosclerotic lesions occurring at otherwise difficult treatment locations. Both FIGS. 22 and 23 depict an osteal stenotic lesion (i.e., a lesion occurring in the area of the origin of a branch in an artery). In FIG. 22, the guide wire 90 is advanced through the primary artery 14 into the branch artery 15. A positioning wire 70 is then selected having a mild curvature of the distal positioning segment 72. Removal of the stenotic material 12 can thus be accomplished without contact of the abrasive segment 40 with the wedge-shaped junction 16 in the artery. In contrast, conventional burr atherectomy devices such as that described in the Auth patent identified above would place significant pressure on the wedge-shaped junction 16 in order to properly position and urge the burr against stenotic material in the branch artery 15.

In FIG. 23, an alternate position of the device of the invention is shown. In this embodiment, the guide wire 90 remains in the main artery, and the positioning wire 70 includes a distal positioning segment 72 having a more sharply arcuate form, permitting engagement of the abrasive segment 40 against the atheroma 12 without placing any pressure with the rotating abrasive segment on the wedge-shaped junction 16.

The abrasive drive shaft device of the invention is particularly well suited for use with intravascular ultrasound imaging technology. As illustrated in FIG. 24, an intravascular ultrasound imaging catheter 100 may be advanced over the guide wire 90 through the first lumen 24 of the catheter 20. Ultrasound transducer elements 102 (indicated schematically) can then be positioned adjacent to the abrasive segment 40 in the same cross-sectional plane of the passageway, permitting imaging of the thickness and composition of the atherosclerotic plaque, the relative position of the abrasive segment of the drive shaft with respect to the stenotic tissue, and imaging of the stenotic tissue as it is being removed.

FIG. 25 illustrates both the utility of this imaging technique and the rotational directional control of the entire device within an artery. FIG. 25A shows in cross section an artery with an atherosclerotic lesion 12 partially obstructing blood flow in an artery 10. The abrasive drive shaft device of the invention has been advanced into location for removal of the lesion 12. The ultrasound imaging elements 102 of the intravascular ultrasound imaging catheter 100 have been positioned in the same cross-sectional plane of the artery as the abrasive segment 40. As can be easily seen in FIG. 25A, the catheter 20 has been positioned rotationally in the artery so that the intravascular ultrasound imaging catheter 100 is lying directly above the ultrasound imaging catheter 100. Rotation of the catheter allows one to move the abrasive segment and ultrasound imaging elements 102 rotationally within the artery to position the abrasive segment against the tissue desired to be removed. Thus, one can not only selectively position the abrasive segment 40 laterally with respect to the guide wire 90 (by selecting the appropriate positioning wire 70) but can also control the rotational position of the abrasive segment 40 within the artery by rotation of the catheter 20 and the positioning wire 70.

FIG. 25B illustrates the expected ultrasound image generated by the intravascular ultrasound imaging catheter 100. The abrasive segment 40 provides an echo 40' and casts a shadow 42 which clearly locate the position of the abrasive segment 40 with respect to the stenosis 12 and to the intravascular ultrasound imaging catheter 100. The depth of the atherosclerotic lesion 12 is also visible. Viewing the ultrasound image, therefore, permits accurate rotational positioning of the abrasive segment 40 within the artery to selectively position the abrasive segment 40 only against tissue desired to be removed and to monitor the progress of stenotic lesion removal throughout the procedure.

As described above, preferably the intravascular ultrasound imaging device comprises a commercially available intravascular ultrasound imaging catheter advanced over the guide wire to a position adjacent to the abrasive segment. Such intravascular ultrasound catheters are available, e.g., from Cardiovascular Imaging Systems, Inc. (Sunnyvale, Calif.), Boston Scientific Corp. (Watertown, Mass.), and Endosonics, Inc. (Pleasanton, Calif.). To the extent that ultrasonic imaging guide wires become commercially available, they could easily be used in lieu of the conventional guide wire and intravascular ultrasound imaging catheter depicted in the drawings.

Conventional fluoroscopic imaging techniques (with or without radio-opaque contrast solution injections) should also be utilized in performing the abrasive drive shaft procedure. The longitudinal and rotational positioning of the device within the artery may be assisted by placing special radio-opaque markings on the elements of the device. For this purpose, as illustrated in FIGS. 26 and 27, conventional radio-opaque markings 104 and 105 can be placed respectively on the positioning wire 70 and the catheter 20. On a positioning wire, such markings may simply comprise a thin layer of gold, platinum or similar radio-opaque material. Similar conventional markings (such as gold or platinum rings) can be placed on other components, and/or components can themselves be manufactured from radio-opaque materials.

FIGS. 28-34 depict a variety of possible shapes for the distal positioning segment 72 of the positioning wire 70. These positioning segments are respectively identified as 72a, 72b, 72c, 72d, 72e, 72f, and 72g. The shapes shown in FIGS. 33 and 34 are essentially similar to one another except that the positioning segment in FIG. 34 will displace the abrasive segment further laterally away from the guide wire than the positioning segment shown in FIG. 33. FIGS. 28-32 provide shapes giving a variety of angular orientations within the artery—i.e., it is possible using such shapes to orient the abrasive segment 40 along an axis that is not parallel to the axis of the guide wire 90. This provides great flexibility for selectively removing stenotic tissue (such as is illustrated in FIGS. 23-24).

FIGS. 35-37 illustrate three possibilities for forming the distal end 74 of the positioning wire. FIG. 35 illustrates in cross-section a simple helical coil formed by the distal portion of the positioning wire 70. The windings of the helical coil together define a central cylindrical opening sized to receive the shaft 96 of the guide wire 90 therein. In FIG. 36, the outer surface of the coiled distal portion 74 has been machined so as to taper it distally inwardly. Such a configuration presents a lower profile while being advanced through the artery. FIG. 37 illustrates another embodiment where both the outer surface and the inner surface of the coil have been machined to present generally flat inner and outer surfaces.

FIGS. 38-40 present alternate embodiments for slidably securing the distal end of the positioning wire 70 to the guide wire 90. A guide 76 is secured to the distal end of the positioning wire 70, the guide 76 including a guiding lumen 77 in which the shaft 96 of the guide wire may be slidably disposed. FIGS. 39 and 39A illustrate one embodiment of such a guide 76' in which the upper portion, through which the distal end of the positioning wire 70 is disposed and secured, has an intermediate void portion leaving part of the positioning wire 70 exposed—in some circumstances, this configuration may be easier to manufacture than the more solid configuration illustrated in FIGS. 38 and 38A. Alternately, as shown in FIGS. 40 and 40A, the guide 76" may have a generally "H"-shaped cross-sectional profile, the upper portion of which is securely attached to the distal end of the positioning wire 70, and the lower portion of which is slidably received over the guide wire shaft 96. Other suitable configurations may also be utilized.

The guide wire 90, the positioning wire 70, and the guide 76 all can be provided with a slippery surface coating such as TEFLON ®, silicone, a combination of silicone over TEFLON ®, or similar slippery material. A particularly slippery surface can be obtained by utilizing PHOTOLINK TM brand surface modification commercially available from Bio-Metric Systems, Inc. of Eden Prairie, Minn.

FIGS. 41-43 illustrate an alternate embodiment of the invention in which a stop 98 is securely attached near the distal end of the guide wire shaft 96. The positioning wire 70 can be advanced until the distal end portion 74 of the positioning wire 70 engages the stop 98; at this point, further advancement of the positioning wire 70 will cause the distal positioning segment 72 of the positioning wire 70 to flex laterally outwardly, thereby increasing the distance between the abrasive segment 40 and the guide wire shaft 96. This configuration provides greater flexibility for controlling the lateral position of the abrasive segment within the artery without having to exchange positioning wires 70.

The catheter 20 can be made from conventional catheter materials, including flexible thermoplastic or silicone materials. For example, the catheter preferably is made from a slippery material such as TEFLON ®, and can be reinforced with an outer layer made of nylon or other similar materials having desirable torque transmitting characteristics. FIG. 44 illustrates a catheter 20 that includes mesh reinforcement 28 (thin wire braiding) along substantially its entire length to improve the torque response of the catheter, reducing the likelihood of "whip" or "ratcheting" of the catheter as it is rotated in the artery to selectively locate the abrasive segment against the stenosis. FIG. 44A is a cross-sectional view illustrating that third and fourth lumens 29 and 30 can be provided for delivery or suction of fluids through the catheter (such as saline, radio-opaque contrast solutions, blood and the like).

Figure 45:
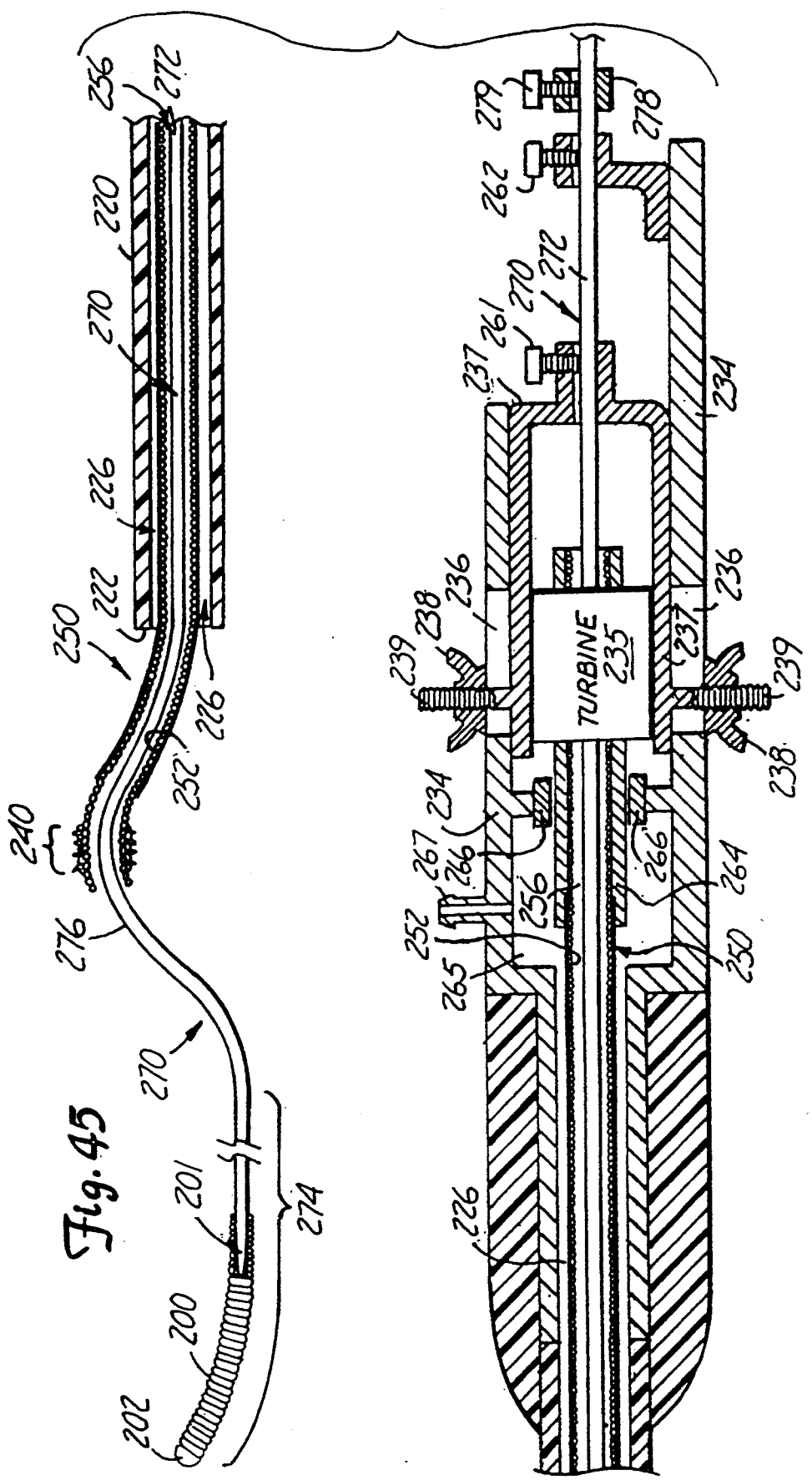
FIG. 45 is a partially broken away view of an alternate embodiment of the invention, shown somewhat schematically and in cross-section, with a rotational atherectomy device of the invention advanced over the guide wire, and with the abrasive segment of the drive shaft located over the positioning segment of the guide wire.

A second general embodiment of the abrasive drive shaft device of the invention is illustrated in FIGS. 45-55 (the various embodiments of the abrasive drive shaft, the various concepts of bonding abrasive material onto the abrasive segment of the drive shaft, and the modifications of the diameters of the drive shaft and positioning wire shown in FIGS. 2–12 are equally applicable to this second general embodiment). In this embodiment the drive shaft is advanced directly over a specially configured guide wire 270, dispensing with the need for the positioning wire of the first embodiment described above and shown in FIGS. 1–44. FIG. 45 illustrates the principal components of the second embodiment of the invention. An elongated catheter 220 includes at least one lumen 226. In this lumen 226 of the catheter 220, a multistrand helically wound flexible drive shaft 250 is disposed. The flexible drive shaft 250 is generally comprised of a helical coil 252. Near its distal end, the drive shaft 250 includes an abrasive segment 240. The distal portion of the drive shaft 250, at least proximally to the abrasive segment 240, is preferably encased in a thin, flexible Teflon ® sheath 254.

A guide wire 270, specially configured and arranged for selective removal of atherosclerotic tissue that is located predominantly on one side of an arterial wall, is disposed in the lumen 256 of the flexible drive shaft 250. The guide wire 270 includes a flexible, generally straight, proximal portion 272, a conventional flexible distal tip portion 274, and a flexible intermediate abrasive drive shaft positioning segment 276 which has a predetermined curved shape. The shape illustrated in FIG. 45 is such that the abrasive segment 240 of the drive shaft is positioned laterally away from the longitudinal axes of the proximal and distal portions 272 and 274, respectively, of the guide wire 270.

The proximal portion of the catheter 220, as shown in the lower half of FIG. 45, is secured to a housing 234. A turbine 235 (or equivalent source for rotational motion) is secured to a turbine mount 237 slidably received in the housing 234. Relative longitudinal sliding movement of the turbine mount 237 with respect to the housing 234 is permitted, and, when it is desired to lock the longitudinal position of the turbine 235 and turbine mount 237 with respect to the housing 234, wing nuts 238 can be tightened on threaded bolts 239 (which extend from the turbine mount 237 through slots 236 in the housing 234). Alternately, equivalent means may be used to prevent relative longitudinal movement of the turbine and turbine mount with respect to the housing.

The turbine 235 is connected by way of turbine link 264 to the flexible drive shaft 250. A conventional seal 266 may be provided against the outer surface of the turbine link 264, preventing fluid from escaping from the cavity 265 while permitting rotational and longitudinal movement of the flexible drive shaft 250 and the turbine linkage 264. A side port 267 may be provided to permit infusion of lubricating fluid (saline or glucose solutions and the like) or radio-opaque contrast solutions into the cavity 265 and the lumen 226 of the catheter 220. The side port 267 could also be connected to a vacuum source for aspiration of fluid through the catheter's lumen 226.

Set screws 261 and 262 are provided to selectively permit or prevent relative longitudinal movement of the guide wire 270 with respect to the turbine mount 237 and with respect to the housing 234. Thus, if the set screw 262 is loosened while the screw 261 is tightened against the guide wire, the guide wire 270 and the flexible drive shaft 250 (which is rigidly connected to the turbine 235 and hence to the turbine mount 237) can be advanced and retracted as a unit with respect to the catheter 220 and the housing 234. Alternately, loosening of set screw 261 and tightening of set screw 262 will permit relative longitudinal movement of the flexible drive shaft and the abrasive segment with respect to the guide wire 270 allowing one to locate the abrasive segment 240 of the drive shaft 250 at an appropriate place on the positioning segment 276 of the guide wire 270. When both set screws 261 and 262 are loosened then obviously one can move the guide wire 270 longitudinally with respect to both the catheter 220 and the flexible drive shaft (and, hence, the abrasive segment).

A guide wire handle 278 can be secured to the proximal end portion of the guide wire 270 by set screw 279 to facilitate rotation of the guide wire 270 with respect to the catheter 220 (and thus the patient's artery, so long as the catheter 220 and housing 234 are not rotated). Set screws 261 and 262 must be loosened to permit such rotational movement; tightening either of such set screws will secure the guide wire rotationally with respect to the housing 234 and catheter 220.

Although the means for securing the guide wire 270, the turbine mount 237, and the housing 234 with respect to one another are illustrated in the drawing as being accomplished by use of wing nuts 238 and set screws 261 and 262, it will be appreciated that other conventional means or mechanisms (such as cam friction fittings, and the like) may easily be employed. Similarly, the guide wire handle 278 can be secured to the guide wire using such cam friction type or equivalent mechanisms. Moreover, the connection of the proximal end of the catheter 220 to the housing 234, as well as the side port 267, are shown somewhat schematically—any of a variety of conventional fittings that are readily commercially available or adaptable for this purpose may easily be employed.

FIGS. 46–51 illustrate the operation and function of the invention for removing an atherosclerotic lesion or atheroma 212 from an artery 210. As indicated above, the guide wire of the invention is particularly useful in removing asymmetrical stenotic lesions, such as the one illustrated in FIGS. 46–51. Although the guide wire will work just as well with symmetrical stenotic lesions or only mildly asymmetrical stenotic lesions, the advantages of the invention are best illustrated with respect to an atherosclerotic lesion that is located predominantly on one side of the arterial wall 210.

In FIG. 46, the guide wire 270 has been advanced into the artery 210 until its distal end 274 extends across the stenosis 212. At this point, the abrasive segment 240, flexible drive shaft 250, and the catheter 220 (with the drive shaft 250 disposed in the lumen 226 of the catheter 220), are advanced over the guide wire 270 until the abrasive segment 240 is located longitudinally over the positioning segment 276 of the guide wire 270 and just proximally to the stenotic tissue 212 to be removed. The guide wire 270 is then rotated (if necessary) using the guide wire handle 278 to position the abrasive segment 240 rotationally within the artery 210 to a position where the physician will begin to remove the stenotic tissue 212 (typically at the thickest part of the stenosis).

The flexible drive shaft 250 and abrasive segment 240 are rotated at relatively high speed (typically in the range of about 30,000 RPM to about 600,000 RPM, or even more, depending only on the physical dimension and capabilities of the turbine/motor, guide wire and flexible drive shaft) to selectively remove an inner layer of the stenotic lesion 212. As the abrasive segment 240 is rotated, it is moved distally and proximally (either together with or independent of the guide wire 270 and the catheter 220) in the artery 210, removing a portion of the atherosclerotic plaque 212 as it is moved. The positioning segment 276 causes the abrasive segment 240 to be urged laterally against the stenotic tissue 212. The rotational position of the abrasive segment 240 with respect to the stenotic tissue 212 can be controlled by rotating the guide wire 270 (and thus the positioning segment 276) in the artery 210 using the guide wire handle 278.

In FIG. 47, the abrasive segment 240, together with the guide wire 270 and the catheter 220, has been advanced forward partially across the stenosis 212, having removed a proximal portion of the inner layer of the atherosclerotic plaque 212.

In FIG. 48, all of the inner layer of the stenotic lesion 212 within reach of the abrasive segment 240 and the positioning segment 276 of the guide wire 270 has been removed. The removal of all of the inner layer of the atherosclerotic plaque 212 from the circumference of the artery may require rotation of the guide wire to several rotational positions, followed by successive distal and proximal movement of the abrasive segment 240 and guide wire 270 at each such rotational position. After all of this inner layer of the stenotic lesion has been removed, there is no significant further pressure of the abrasive segment 240 against the atherosclerotic lesion 212. Consequently, as illustrated in FIGS. 49-50, the rotational atherectomy device, with the abrasive segment 240, can then be removed from the guide wire 270 and replaced with a different rotational atherectomy device having a larger diameter flexible drive shaft 250 with a larger diameter abrasive segment 240, allowing one to remove the outer layer of atherosclerotic plaque 212. More of the atherosclerotic lesion 212 can then be removed, as illustrated in FIG. 51. When a sufficient amount of the lesion 212 has been removed, the entire device, including the guide wire, can be withdrawn.

Conventional fluoroscopic imaging techniques (with or without radio-opaque contrast solution injections) should be utilized in performing the directional rotational atherectomy procedure. The longitudinal and rotational positioning of the guide wire 270 and the abrasive segment 240 within the artery 210 may be assisted by placing special radio-opaque markings on the guide wire 270. For this purpose, as illustrated in FIG. 53, a conventional radio-opaque marking 280 can be placed on the positioning segment 276 of the guide wire 270. Such markings may simply comprise a thin layer of gold, platinum or similar radio-opaque material.

The positioning segment 276 of the guide wire 270 can be configured into a variety of suitable shapes with varying maximal heights of its curve to provide control over the degree of lateral deflection of the abrasive segment 240 when it is positioned over the positioning segment. FIG. 52 illustrates a typical configuration. Preferably the positioning segment is generally co-planar; i.e., the curves of this segment are all made in the same plane so that, as viewed in the drawings, the wire would lie flat. The curves of the positioning segment preferably are formed so that the longitudinal axis 297 of the positioning segment 276 at its point of greatest deflection is spaced a distance $H_1$ laterally to one side of the longitudinal axis 292 of the proximal portion 272 of the guide wire 270. It is this lateral displacement of the positioning segment 276 that provides control over the degree of lateral displacement of the abrasive segment 240 within the artery. Accordingly, rotation of the guide wire (when the abrasive segment is located over the distal positioning segment) provides directional control over the rotational position of the abrasive segment 240 within the artery. The distance $H_1$ is selected based on the relative size of the artery and the degree of stenosis, as well as the diameter of the (abrasive) drive shaft selected to be used. Guide wires having smaller $H_1$ distances are useful in smaller arteries and arteries with tighter stenoses. Conversely, guide wires with larger $H_1$ distances are useful in larger passageways and those with lesser degrees of stenosis.

Although the preferred amount of deflection provided by the positioning segment 276 will vary from one application to another, preferably the curved positioning segment 276 is shaped so that when the abrasive segment 240 is positioned over the point of greatest deflection of such segment 276, the axis of the abrasive segment 240 (or at least the portion of the abrasive segment located over such point of greatest deflection) is positioned away from one or both of the longitudinal axes 292 and 294 of the proximal and the distal end portions of the guide wire 270 by a distance not less than about one half the diameter of the guide wire 270, and, more preferably, not less than about the diameter of the guide wire 270 (measured at the distal positioning segment 276 of the guide wire 270). The range of deflection most preferred in coronary arteries typically will be from about 0.5 mm to about 3.5 mm. In larger peripheral arteries (such as the iliac or femoral arteries), the maximum amount of deflection can be up to about 8 mm.

In the preferred embodiment shown in FIG. 52, the longitudinal axis 292 of the proximal portion 272 of the guide wire 270 is not coaxial with the longitudinal axis 294 of the distal portion 274 of the guide wire. As can be seen by reference to FIG. 47, during the procedure the outer surface of the catheter 220 lies against the inner wall of the artery 210, as does the distal portion 274 of the guide wire 270. Preferably the guide wire is formed so that the longitudinal axis 294 of the distal portion 274 of the guide wire is offset from the longitudinal axis 292 of the proximal portion 272 by a distance $H_2$, which is equal to the distance, measured near the distal end 222 of the catheter 220, from the outer surface of the guide wire's proximal portion 272 to the outer surface of the catheter 220, thus accounting for the fact that the proximal portion of the guide wire 270 is contained within the drive shaft and catheter, while the distal portion of the guide wire abuts directly the artery wall.

FIG. 54 illustrates an alternate configuration where the proximal portion 272 of the guide wire 270 is generally coaxial with the proximal portion of the distal positioning segment 276. FIG. 55 shows yet another embodiment where the distal end portion 274 is generally coaxial with the distal portion of the distal positioning segment 276. Other guide wire configurations also may be utilized, the characteristic feature of any such configuration being that it provides lateral displacement of the abrasive segment when the abrasive segment is located over the distal positioning segment of such guide wire.

The shaft of the guide wire preferably is made of a shape-memory alloy, such as nitinol. The fabrication of the guide wire shaft from such a shape-memory alloy assures preservation of the configuration of the intermediate distal positioning segment 276 of the guide wire 270 even after it is advanced around very tortuous curves in the body passageway.

The distal portion 274 of the guide wire 270 includes a conventional relatively flexible, helical coil 200 having a proximal end which is secured to the guide wire shaft near the shaft's distal end. A rounded tip 202 is attached to the distal end of the helical coil 200. The distal end portion 201 of the guide wire shaft, disposed within the helical coil 200, may be tapered to provide greater flexibility to the distal tip portion of the guide wire. The distal end of the guide wire shaft may be attached directly to the rounded tip 202. Alternately, as shown in FIG. 54, the distal end of the guide wire shaft may terminate short of the rounded tip 202 and be connected to the tip 202 by a safety wire 203. Such helical coil flexible distal guide wire tips are well known, such as those shown in U.S. Pat. Nos. 4,554,929 (Re. 33,911); 4,984,581; 4,799,496; and 5,069,217. The coil preferably is made of a radio-opaque material such as titanium or platinum, or alloys of these metals. The coil also may be made of stainless steel covered with coatings of radio-opaque material such as titanium, tungsten, platinum, or alloys thereof. The coil may be attached to the guide wire shaft and the rounded tip by conventional means, such as welding, soldering, brazing or suitable adhesives (typically epoxies or cyanoacrylates).

While a preferred embodiment of the present invention has been described, it should be understood that various changes, adaptations and modifications may be made therein without departing from the spirit of the invention and the scope of the appended claims.

What is claimed is:

1. An abrasive drive shaft atherectomy device comprising:
   a rotational atherectomy apparatus having a flexible, elongated drive shaft with proximal and distal ends, the drive shaft including a segment, near its distal end, coated with an abrasive material to define an abrasive segment of the drive shaft, the drive shaft further including a central lumen for receipt of a guide wire therein, around which the drive shaft may be rotated; and
   a guide wire having a flexible, generally straight proximal portion, a flexible distal end portion, each such portion having a longitudinal axis, the longitudinal axis of at least a portion of the flexible distal end portion being normally substantially parallel to the longitudinal axis of the proximal portion, and a flexible intermediate positioning segment, the positioning segment having a predetermined curved shape so that when the abrasive segment of the drive shaft is advanced over the guide wire to a position along the curved positioning segment, such curved segment positions the abrasive segment laterally away from one or both of such longitudinal axes.

2. The device of claim 1 wherein the abrasive material comprises a plurality of abrasive particles which are secured directly to the drive shaft by a bonding material.

3. The device of claim 2 wherein the abrasive particles are at least partially embedded in the bonding material, the thickness of the bonding material between substantially all of the abrasive particles and the drive shaft being not more than about 20 $\mu$m.

4. The device of claim 2 wherein the abrasive particles are at least partially embedded in the bonding material, the thickness of the bonding material between substantially all of the abrasive particles and the drive shaft being not more than about 5 $\mu$m.

5. The device of claim 1 wherein the abrasive material comprises diamond chips having a largest dimension of substantially 30 $\mu$m or less.

6. The device of claim 1 wherein the abrasive material comprises diamond chips having a largest dimension of substantially 20 $\mu$m or less.

7. The device of claim 1 wherein the coating of abrasive material is not thicker than about 50 $\mu$m.

8. The device of claim 1 wherein the coating of abrasive material is not thicker than about 25 $\mu$m.

9. The device of claim 1 wherein the diameter of the abrasive segment is not more than about 100 $\mu$m larger than the diameter of the drive shaft just proximal to the abrasive segment.

10. The device of claim 1 wherein the diameter of the abrasive segment is not more than about 50 $\mu$m larger than the diameter of the drive shaft just proximal to the abrasive segment.

11. The device of claim 2 wherein the drive shaft comprises at least one helically wound wire, the bonding material being applied to adjacent turns of the helically wound wire to secure the abrasive material to such turns and to secure at least some of such adjacent turns to one another.

12. The device of claim 11 wherein the bonding material is applied to two or more sub-segments of the abrasive segment, such sub-segments being spaced from one another by at least one turn of the helically wound wire which is not secured to either sub-segment by the bonding material, thereby allowing the abrasive segment to flex at such turn of the helically wound wire.

13. The device of claim 2 wherein the drive shaft comprises at least one helically wound wire, the bonding material being applied to adjacent turns of the helically wound wire to secure the abrasive material to such turns without securing any of such adjacent turns to one another.

14. The device of claim 1 wherein the coating of abrasive material is of a generally uniform thickness throughout the length of the abrasive segment.

15. The device of claim 1 wherein the drive shaft includes promixal and distal portions and is comprised of at least one helically wound wire, the proximal portion of the drive shaft having wire turns with a first pitch, and the distal portion having wire turns with a second pitch which is greater than the first pitch.

16. The device of claim 1 wherein the drive shaft comprises at least one helically wound wire, such wire having a generally rectangular cross section and, when helically wound, providing the drive shaft with an outer surface generally flatter than that provided by a wire having a round cross section.

17. The device of claim 1 wherein the drive shaft is comprised of at least one helically wound wire, such wire having a generally round cross section, the drive shaft having a distal portion that includes the abrasive segment, such distal portion being machined, on its outer surface, to a smaller diameter, providing the drive shaft with an outer surface generally flatter than that provided by a wire having a round cross section.

18. The device of claim 1 wherein the drive shaft and guide wire each include a proximal portion having a first diameter and a distal portion having a second, smaller diameter thereby allowing these distal portions to assume a lower profile and to be more flexible.

19. The device of claim 18 wherein the length of such smaller diameter distal portion of the drive shaft is not more than about 20 cm.

20. The device of claim 1 wherein the drive shaft comprises a plurality of helically wound wire strands.

21. The device of claim 20 wherein the drive shaft includes promixal and distal portions, the proximal portion of the drive shaft having wire strands turning with a first pitch, and the distal portion having wire strands turning with a second pitch which is greater than the first pitch.

22. An abrasive drive shaft atherectomy device, comprising:
 an elongated catheter having at least first and second lumens and a distal end;
 a guide wire receivable in the first lumen of the catheter and extending distally therefrom;
 a flexible, elongated drive shaft having proximal and distal ends and a central lumen, the drive shaft being receivable in the second lumen of the catheter and being longitudinally movable therein, the drive shaft further including a segment, near its distal end, coated with an abrasive material to define an abrasive segment of the drive shaft; and
 a positioning wire, which is receivable in the drive shaft lumen and around which the drive shaft may be rotated, the positioning wire having a distal end and means for slidably securing the distal end of the positioning wire about the guide wire distally of the distal end of the catheter so that the positioning wire can be moved proximally and distally with respect to the guide wire, the positioning wire further including a distal positioning segment having a predetermined shape, the drive shaft being movable longitudinally with respect to the positioning wire and the catheter to selectively locate the drive shaft's abrasive segment along the predetermined shape of such positioning segment of the positioning wire;
 at least the proximal portion of the positioning segment of the positioning wire being retractable into and advanceable out of the catheter, the predetermined shape of the positioning segment of the positioning wire being curved so that when the abrasive segment is positioned along such curve and such proximal portion of the positioning segment is retracted into the catheter, the abrasive segment will be drawn to a position close to the guide wire, and when the proximal portion of the curved positioning segment of the positioning wire is advanced out of the catheter the predetermined curved shape of the positioning segment spaces the abrasive segment laterally further away from the guide wire.

23. The device of claim 22 wherein the abrasive material comprises a plurality of abrasive particles which are secured directly to the drive shaft by a bonding material.

24. The device of claim 23 wherein the abrasive particles are at least partially embedded in the bonding material, the thickness of the bonding material between substantially all of the abrasive particles and the drive shaft being not more than about 20 $\mu$m.

25. The device of claim 23 wherein the abrasive particles are at least partially embedded in the bonding material, the thickness of the bonding material between substantially all of the abrasive particles and the drive shaft being not more than about 5 $\mu$m.

26. The device of claim 22 wherein the abrasive material comprises diamond chips having a largest dimension of substantially 30 $\mu$m or less.

27. The device of claim 22 wherein the abrasive material comprises diamond chips having a largest dimension of substantially 20 $\mu$m or less.

28. The device of claim 22 wherein the coating of abrasive material is not thicker than about 50 $\mu$m.

29. The device of claim 22 wherein the coating of abrasive material is not thicker than about 25 $\mu$m.

30. The device of claim 22 wherein the diameter of the abrasive segment is not more than about 100 $\mu$m larger than the diameter of the drive shaft just proximal to the abrasive segment.

31. The device of claim 22 wherein the diameter of the abrasive segment is not more than about 50 $\mu$m larger than the diameter of the drive shaft just proximal to the abrasive segment.

32. The device of claim 23 wherein the drive shaft comprises at least one helically wound wire, the bonding material being applied to adjacent turns of the helically wound wire to secure the abrasive material to such turns and to secure at least some of such adjacent turns to one another.

33. The device of claim 32 wherein the bonding material is applied to two or more sub-segments of the abrasive segment, such sub-segments being spaced from one another by at least one turn of the helically wound wire which is not secured to either sub-segment by the bonding material, thereby allowing the abrasive segment to flex at such turn of the helically wound wire.

34. The device of claim 23 wherein the drive shaft comprises at least one helically wound wire, the bonding material being applied to adjacent turns of the helically wound wire to secure the abrasive material to such turns without securing any of such adjacent turns to one another.

35. The device of claim 22 wherein the coating of abrasive material is of a generally uniform thickness throughout the length of the abrasive segment.

36. The device of claim 22 wherein the drive shaft includes promixal and distal portions and is comprised of at least one helically wound wire, the proximal portion of the drive shaft having wire turns with a first pitch, and the distal portion having wire turns with a second pitch which is greater than the first pitch.

37. The device of claim 22 wherein the drive shaft comprises at least one helically wound wire, such wire having a generally rectangular cross section and, when helically wound, providing the drive shaft with an outer surface generally flatter than that provided by a wire having a round cross section.

38. The device of claim 22 wherein the drive shaft is comprised of at least one helically wound wire, such wire having a generally round cross section, the drive shaft having a distal portion that includes the abrasive segment, such distal portion being machined, on its outer surface, to a smaller diameter, providing the drive shalt with an outer surface generally flatter than that provided by a wire having a round cross section.

39. The device of claim 22 wherein the drive shaft and positioning wire each include a proximal portion having a first diameter and a distal portion having a second, smaller diameter thereby allowing these distal portions to assume a lower profile and to be more flexible.

40. The device of claim 39 wherein the length of such smaller diameter distal portion of the drive shaft is not more than about 20 cm.

41. The device of claim 22 wherein the drive shaft comprises a plurality of helically wound wire strands.

42. The device of claim 41 wherein the drive shaft includes promixal and distal portions, the proximal portion of the drive shaft having wire strands turning with a first pitch, and the distal portion having wire strands turning with a second pitch which is greater than the first pitch.

43. The directional rotational atherectomy device of claim 22 further comprising intravascular ultrasound imaging catheter means advancable over the guide wire to a position adjacent the abrasive segment of the drive shaft for providing a cross-sectional image of tissue of interest and of the position of the abrasive segment with respect to such tissue.

44. The directional rotational atherectomy device of claim 43 including means for securing the intravascular ultrasound imaging catheter with respect to the drive shaft so that the intravascular ultrasound imaging catheter and drive shaft can be advanced and retracted as a unit with respect to the tissue of interest.

45. The directional rotational atherectomy device of claim 22 wherein the guide wire includes intravascular ultrasonic imaging means for providing a cross-sectional image of tissue of interest and of the position of the abrasive segment of the drive shaft with respect to such tissue.

46. An abrasive drive shaft atherectomy device comprising:
a rotational atherectomy apparatus having a flexible, elongated drive shaft with proximal and distal ends, the drive shaft being comprised of a plurality of helically wound wire strands and including a segment, near its distal end, coated with an abrasive material of a generally uniform thickness to define an abrasive segment of the drive shaft, the abrasive material comprising diamond chips having a largest dimension of substantially 30 $\mu$m or less, the diamond chips being secured directly to the drive shaft by a bonding material, the diameter of the abrasive segment being not more than about 100 $\mu$m larger than the diameter of the drive shaft just proximal to the abrasive segment, the diamond chips being at least partially embedded in the bonding material, the thickness of the bonding material between substantially all of the diamond chips and the drive shaft being not more than about 20 $\mu$m, the drive shaft further including a central lumen for receipt of a guide wire therein, around which the drive shaft may be rotated; and
a guide wire having a flexible, generally straight proximal portion, a flexible distal end portion, each such portion having a longitudinal axis, and a flexible intermediate positioning segment, the positioning segment having a predetermined curved shape such that when the abrasive segment of the drive shaft is advanced over the guide wire to a position along the curved positioning segment, such curved segment positions the abrasive segment laterally away from one or both of such longitudinal axes.

47. An abrasive drive shaft atherectomy device, comprising:
an elongated catheter having at least first and second lumens and a distal end;
a guide wire receivable in the first lumen of the catheter and extending distally therefrom;
a flexible, elongated drive shaft having proximal and distal ends and a central lumen, the drive shaft being receivable in the second lumen of the catheter and being longitudinally movable therein, the drive shaft being comprised of a plurality of helically wound wire strands and including a segment, near its distal end, coated with an abrasive material of a generally uniform thickness to define an abrasive segment of the drive shaft, the abrasive material comprising diamond chips having a largest dimension of substantially 30 $\mu$m or less, the diamond chips being secured directly to the drive shaft by a bonding material, the diameter of the abrasive segment being not more than about 100 $\mu$m larger than the diameter of the drive shaft just proximal to the abrasive segment, the diamond chips being at least partially embedded in the bonding material, the thickness of the bonding material between substantially all of the diamond chips and the drive shaft being not more than about 20 $\mu$m; and
a positioning wire, which is receivable in the drive shaft lumen and around which the drive shaft may be rotated, the positioning wire having a distal end and means for slidably securing the distal end of the positioning wire about the guide wire distally of the distal end of the catheter so that the positioning wire can be moved proximally and distally with respect to the guide wire, the positioning wire further including a distal positioning segment having a predetermined shape, the drive shaft being movable longitudinally with respect to the positioning wire and the catheter to selectively locate the drive shaft's abrasive segment along the predetermined shape of such positioning segment of the positioning wire to selectively position the abrasive segment laterally of the guide wire.

* * * * *